US00RE41439E

(19) United States
(12) Reissued Patent
Miller et al.

(10) Patent Number: US RE41,439 E
(45) Date of Reissued Patent: Jul. 13, 2010

(54) PHARMACEUTICAL COMPOSITIONS AND METHODS FOR USE

(75) Inventors: Craig Harrison Miller, Winston-Salem, NC (US); Gary Maurice Dull, Lewisville, NC (US); Lan Miao, Advance, NC (US); Dwo Lynm, Winston-Salem, NC (US); Jeffrey Daniel Schmitt, Asheville, NC (US); Thomas Jeff Clark, Elon, NC (US)

(73) Assignee: Targacept, Inc., Winston-Salem, NC (US)

(21) Appl. No.: 11/702,484

(22) Filed: Feb. 5, 2007

Related U.S. Patent Documents

Reissue of:
(64) Patent No.: 6,852,721
Issued: Feb. 8, 2005
Appl. No.: 09/864,905
Filed: May 24, 2001

U.S. Applications:
(63) Continuation-in-part of application No. 09/578,768, filed on May 25, 2000, now Pat. No. 6,440,970.

(51) Int. Cl.
*C07D 487/08* (2006.01)
*C07D 209/00* (2006.01)
*A61K 31/40* (2006.01)
*A61P 25/00* (2006.01)

(52) U.S. Cl. ..... 514/249; 514/300; 544/349; 546/122

(58) Field of Classification Search ..... 544/349; 546/122; 514/249, 300
See application file for complete search history.

(56) References Cited

U.S. PATENT DOCUMENTS

| | | | | |
|---|---|---|---|---|
| 5,478,939 A | * | 12/1995 | Trybulski et al. | 544/336 |
| 5,510,355 A | | 4/1996 | Bencherif et al. | 514/305 |
| 5,817,679 A | | 10/1998 | Shen et al. | 514/339 |
| 5,852,041 A | | 12/1998 | Cosford et al. | 514/351 |
| 5,853,696 A | | 12/1998 | Elmaleh et al. | 424/185 |
| 5,922,723 A | | 7/1999 | Bencherif et al. | 514/256 |
| 5,952,339 A | | 9/1999 | Bencherif et al. | 514/294 |
| 5,969,144 A | | 10/1999 | London et al. | 546/276.7 |
| 6,022,868 A | | 2/2000 | Olesen et al. | 514/210 |
| 6,060,473 A | | 5/2000 | Shen et al. | 514/253 |
| 6,635,645 B1 | | 10/2003 | Lochead et al. | 514/252.01 |
| 7,265,115 B2 | * | 9/2007 | Bunnelle et al. | 514/248 |

FOREIGN PATENT DOCUMENTS

| | | | |
|---|---|---|---|
| JP | 7-61940 | | 3/1995 |
| WO | WO 96/30372 A1 | | 10/1996 |
| WO | WO 97/11072 | | 3/1997 |
| WO | WO 97/13770 | | 4/1997 |
| WO | WO97/40049 | * | 10/1997 |
| WO | WO 98/54182 | | 12/1998 |
| WO | WO 00/44755 | | 8/2000 |
| WO | WO 00/58311 | | 10/2000 |
| WO | WO00/66586 | * | 11/2000 |

OTHER PUBLICATIONS

Amy H. Fix, Attorney for Applicants: Attachment: Marked–up copy of the claims submitted Dec. 19, 2007, pp. 2–12.*

Viltemagna et al., "Nicotine and Related Compounds as PET and SPECT Ligunds," Neuocal Nicotinic Receptors: Pharmacology and Therapeutic Opportunities, 1998, pp. 235–250.

Barlocco et al., "Mono– and Disubstituted –3–8–diazabicycle [3.2.1]octane Derivatives as Analgesics Structurally Related to Epitaidine: Synthesis, Activity, and Modeling," J. Med Chem, vol. 41, 1998, pp. 674–681.

Cheng et al., "Synthesis and binding of 6,7,8, 9–tetrahydro–5H–pyrido[3,4–α]azepine and related ring–opened analogs at central nicotine receptors," Eur. J. Med. Chem, vol. 34, 1999, pp. 177–190.

Williams et al., "Neuronal Nicotinic Acetylcholine Receptors," DN&P, vol. 7, No. 4, May 1994, pp. 205–223.

Badio et al., "Synthesis and nicotinic activity of aplboxidine: an isoxazole analogue of epibatidine," European Journal of Pharmacology, vol. 321, No. 2, 1997, pp. 180–194.

Olive et al., "Synthesis of New Open–Ring and homo–Epibatidine Analogues from Tropinone," J. Org. Chem, 3 pages.

International Search Report for PCT/US01/16941.*

* cited by examiner

*Primary Examiner*—Susanna Moore
(74) *Attorney, Agent, or Firm*—Womble Carlyle Sandridge & Rice, PLLC; Amy H. Fix

(57) ABSTRACT

The present invention relates to diazabicyclic compounds, preferably to N-aryl diazabicyclic compounds. Of particular interest are 2-pyridinyl diazabicyclic compounds, such as (1S,4S)-2-(5-(3-methoxyphenoxy)-3-pyridyl)-2,5-diazabicyclo[2.2.1]heptane. Other exemplary compounds of the present invention include (1S,4S)-2-(5-(4-methoxyphenoxy)-3-pyridyl)-2,5-diazabicyclo[2.2.1]heptane, (1S,4S)-2-(5-(3-thienyl)-3-pyridyl)-2,5-diazabicyclo[2.2.1]heptane, (1S,4S)-2-(5-(4-fluorophenoxy)-3-pyridyl)-2,5-diazabicyclo[2.2.1]heptane, and (1S,4S)-2-(5-benzoyl-3-pyridyl)-2,5-diazabicyclo[2.2.1]heptane. The present invention also relates to prodrug derivatives of the compounds of the present invention.

31 Claims, No Drawings

PHARMACEUTICAL COMPOSITIONS AND METHODS FOR USE

Matter enclosed in heavy brackets [ ] appears in the original patent but forms no part of this reissue specification; matter printed in italics indicates the additions made by reissue.

RELATED APPLICATION

This application is a CIP of U.S. patent application Ser. No. 09/578,768, filed May 25, 2000, now U.S. Pat. No. 6,440,970, the disclosure of which is incorporated by reference herein in its entirety.

BACKGROUND OF THE INVENTION

The present invention relates to pharmaceutical compositions, particularly pharmaceutical compositions incorporating compounds that are capable of affecting nicotinic cholinergic receptors. More particularly, the present invention relates to compounds capable of activating nicotinic cholinergic receptors, for example, as agonists of specific nicotinic receptor subtypes. The present invention also relates to methods for treating a wide variety of conditions and disorders, particularly conditions and disorders associated with dysfunction of the central and autonomic nervous systems.

Nicotine has been proposed to have a number of pharmacological effects. See, for example, Pullan et al., N. Engl. J. Med. 330:811 (1994). Certain of those effects may be related to effects upon neurotransmitter release. See, for example, Sjak-shie et al., Brain Res. 624:295 (1993), where neuroprotective effects of nicotine are proposed. Release of acetylcholine and dopamine by neurons upon administration of nicotine has been reported by Rowell et al., J. Neurochem. 43:1593 (1984); Rapier et al., J. Neurochem. 50:1123 (1988); Sandor et al., Brain Res. 567:313 (1991) and Vizi, Br. J. Pharmacol. 47:765 (1973). Release of norepinephrine by neurons upon administration of nicotine has been reported by Hall et al., Biochem. Pharmacol. 21:1829 (1972). Release of serotonin by neurons upon administration of nicotine has been reported by Hery et al., Arch. Int. Pharmacodyn. Ther. 296:91 (1977). Release of glutamate by neurons upon administration of nicotine has been reported by Toth et al., Neurochem Res. 17:265 (1992). Confirmatory reports and additional recent studies have included the modulation in the Central Nervous System (CNS) of glutamate, nitric oxide, GABA, takykinins, cytokines and peptides (reviewed in Brioni et al., Adv. Pharmacol. 37:153 (1997). In addition, nicotine reportedly potentiates the pharmacological behavior of certain pharmaceutical compositions used for the treatment of certain disorders. See, for example, Sanberg et al., Pharmacol. Biochem. & Behavior 46:303 (1993); Harsing et al., J. Neurochem. 59:48 (1993) and Hughes, Proceedings from Intl. Symp. Nic. S40 (1994). Furthermore, various other beneficial pharmacological effects of nicotine have been proposed. See, for example, Decina et al., Biol. Psychiatry 28:502 (1990); Wagner et al., Pharmacopsychiatry 21:301 (1988); Pomerleau et al., Addictive Behaviors 9:265 (1984); Onaivi et al., Life Sci. 54(3):193 (1994); Tripathi et al., J. Pharmacol. Exp. Ther. 221:91(1982) and Hamon, Trends in Pharmacol. Res. 15:36 (1994).

Various nicotinic compounds have been reported as being useful for treating a wide variety of conditions and disorders. See, for example, Williams et al., Drug News Perspec. 7(4) :205 (1994); Arneric et al., CNS Drug Rev. 1(1)1: (1995); Arneric et al., Exp. Opin. Invest. Drugs 5(1):79 (1996); Bencherif et al., J. Pharmacol. Exp. Ther. 279:1413 (1996); Lippiello et al., J. Pharmacol. Exp. Ther. 279:1422 (1996); Damaj et al., J. Pharmacol. Exp. Ther. 291:390 (1999); Chiari et al., Anesthesiology 91:1447 (1999); Lavand'homme and Eisenbach, Anesthesiology 91:1455 (1999); Holladay et al., J. Med Chem. 40(28): 4169 (1997); Bannon et al., Science 279: 77 (1998); PCT WO 94/08992, PCT WO 96/31475, PCT WO 96/40682, and U.S. Pat. No. 5,583,140 to Bencherif et al., U.S. Pat. No. 5,597,919 to Dull et al., U.S. Pat. No. 5,604,231 to Smith et al. and U.S. Pat. No. 5,852,041 to Cosford et al. Nicotinic compounds are reported as being particularly useful for treating a wide variety of CNS disorders. Indeed, a wide variety of compounds have been reported to have therapeutic properties. See, for example, U.S. Pat. Nos. 5,1871,166 to Kikuchi et al., U.S. Pat. No. 5,672,601 to Cignarella, PCT WO 99/21834 and PCT WO 97/40049, UK Patent Application GB 2295387 and European Patent Application 297,858.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses, and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransritter receptors, and/or inappropriate interaction between neuroframitters and neurotransmitter receptors). Several CNS disorders can be attributed to a deficiency of choline, dopamine, norepinephrine and/or serotonin. Relatively common CNS disorders include pre-senile dementia (early-onset Alzheimer's disease), senile dementia (dementia of the Alzheimer's type), micro-infarct dementia, AWDS-related dementia, Creutzfeld-Jakob disease, Pick's disease, Parkinsonism including Parkinson's disease, progressive supranuclear palsy, Huntington's chorea, tardive dyskinesia, hyperkinesia, mnania, attention deficit disorder, anxiety, dyslexia, schizophrenia, depression, obsessive-compulsive disorders and Tourette's syndrome.

It would be desirable to provide a useful method for the prevention and treatment of a condition or disorder by administering a nicotinic compound to a patient susceptible to or suffering from such a condition or disorder. It would be highly beneficial to provide individuals suffering from certain disorders (e.g., CNS diseases) with interruption of the symptoms of those disorders by the administration of a pharmaceutical composition containing an active ingredient having nicotinic pharmacology and which has a beneficial effect (e.g., upon the functioning of the CNS), but which does not provide any significant associated side effects. It would be highly desirable to provide a pharmaceutical composition incorporating a compound with interacts with nicotinic receptors, such as those which have the potential to effect the functioning of the CNS, but, when employed in an amount sufficient to effect the fimctioning of the CNS, does not significantly effect those receptor subtypes which have the potential to induce undesirable side effects (e.g., appreciable activity at cardiovascular and skeletal muscle sites).

SUMMARY OF THE INVENTION

The present invention relates to diazabicyclic compounds, and preferably N-aryl diazabicyclic compounds. Of particular interest are certain substituted N-pyridyl diazabicyclic compounds. Exemplary compounds of the present invention include: (1S,4S)-2-(5-(3-methoxyphenoxy)-3-pyridyl)-2,5-diazabicyclo[2.2.1]heptane, (1S,4S)-2-(5-(4-methoxyphenoxy)-3-pyridyl)-2,5-diazabicyclo[2.2.1]heptane, (1S,4S)-2-(5-(4-fluorophenoxy)-3-pyridyl)-2,5-diazabicyclo[2.2.1]heptane, (1S,4S)-2-(5-benzoyl-3-pyridyl)-2,5-diazabicyclo[2.2.1]heptane, and (1S,4S)-2-(5-(3-thienyl)-3-pyridyl)-2,5-diazabicyclo[2.2.1]heptane. The present invention also relates to prodrug derivatives of the compounds of the present invention. The present invention also relates to methods for synthesizing those types of compounds.

The present invention also relates to methods for the prevention or treatment of a wide variety of conditions or disorders, particularly those disorders characterized by dysfunction of nicotinic cholinergic neurotrrnsmission including disorders involving neuromodulation of neurotansmitter release, such as dopamine release. The present invention also relates to methods for the prevention or treatment of disorders, such as central nervous system (CNS) disorders, which are characterized by an alteration in normal neurotransmitter release. The present invention also relates to methods for the treatment of certain conditions (e.g., a method for alleviating pain). The methods involve administering to a subject an effective amount of a compound of the present invention.

The present invention, in another aspect, relates to a pharmaceutical composition comprising an effective amount of a compound of the present invention. Such a pharmaceutical composition incorporates a compound which, when employed in effective amounts, has the capability of interacting with relevant nicotinic receptor sites of a subject, and hence has the capability of acting as a therapeutic agent in the prevention or treatment of a wide variety of conditions and disorders, particularly those disorders characterized by an alteration in normal neurotransmitter release. Preferred pharmaceutical compositions comprise compounds of the present invention.

The pharmaceutical compositions of the present invention are useful for the prevention and treatment of disorders, such as CNS disorders, which are characterized by an alteration of normal neurotranismitter release. The pharmaceutical compositions provide therapeutic benefit to individuals suffering from such disorders and exhibiting clinical manifestations of such disorders in that the compounds within those compositions, when employed in effective amnounts, have the potential to: (i) exhibit nicotinic pharmacology and affect relevant nicotinic receptors sites (e.g.,act as a pharmacological agonist to activate nicotinic receptors), and/or (ii) modulate neurotransmitter secretion and thus prevent and suppress the symptoms associated with those diseases. In addition, the compounds are expected to have the potential to fulfill the following results for the patient: (i) to alter the number of nicotinic cholinergic receptors of the brain of the patient, (ii) to exhibit neuroprotective effects and (iii) to result in no appreciable adverse side effects when administered in effective amounts—side effects such as significant increases in blood pressure and heart rate, significant negative effects upon the gastrointestinal tract, and significant effects upon skeletal muscle. The pharmaceutical compositions of the present invention are believed to be safe and effective with regards to prevention and treatment of a wide variety of conditions and disorders.

The foregoing and other aspects of the present invention are explained in detail in the detailed description and examples set forth below.

DETAILED DESCRIPTION OF THE INVENTION

The compounds of the present invention include compounds having a diazabicyclic ring. The structure can be represented by the formula:

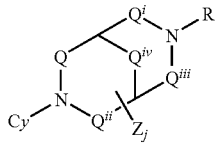

In the structure, Q is $(CH_2)_u$, $Q^i$ is $(CH_2)_v$, $Q^{ii}$ is $(CH_2)_w$, $Q^{iii}$ is $(CH_2)_x$, and $Q^{iv}$ is $(CH_2)_y$, where u, v, w and x are individually 0, 1, 2, 3 or 4, preferably 0 or 1, and y is 1 or 2. R is hydrogen or lower alkyl, preferably hydrogen. In addition, the values of u, v, w, x and y are selected such that the resulting diazabicyclic ring contains 7, 8 or 9 members, preferably 7 members. Z represents a suitable non-hydrogen substituent species; exemplary species are set forth hereinafter. In addition, j is an integer from 0 to 10, preferably 0, 1 or 2.

In the structure, preferably Cy represents a suitably substituted 6-membered aromatic ring, as represented by the formula:

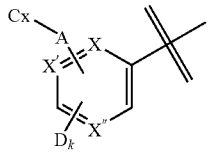

where each of X, X' and X" are individually nitrogen, nitrogen bonded to oxygen (e.g., an N-oxide or other N—O functionality) or carbon bonded to a substituent species (i.e., hydrogen or a non-hydrogen species); A is O (oxygen) or C═O; D is a suitable non-hydrogen substituent species, as set forth hereinafter; k is either 0, 1 or 2, preferably 0 or 1; and Cx is selected from a group consisting of aryl, substituted aryl, heteroaryl, substituted heteroaryl, non-aromatic heterocyclyl, substituted nonaromatic heterocyclyl, non-aromatic heterocyclylalkyl and substituted non-aromatic heterocyclylalkyl. A can also be a covalent bond, with the proviso that when A is so defined, the diazabicyclic ring is not 2,5-diazabicyclo[2.2.1]heptane and/or Cx is not phenyl or substituted phenyl. When A is a covalent bond, it is preferred that Cx is aryl or heteroaryl.

Non-hydrogen substituent species Z and D, as well as those substituent species attached to the various Cx groups, typically have a sigma m value between about −0.3 and about 0.75 and include alkyl, substituted alkyl, alkenyl, substituted alkenyl, nonaromatic heterocyclyl, substituted nonaromatic heterocyclyl, aryl, substituted aryl, heteroaryl, substituted heteroaryl, alkylaryl, substituted alkylaryl, arylalkyl, substituted arylalkyl, —F, —Cl, —Br, —I, —OR', —NR'R", —$CF_3$, —CN, —$N_3$, —$NO_2$, —$C_2R'$, —SR', —SOR', —$SO_2CH_3$, —$SO_2NR'R"$, —C(═O)NR'R", —NR'C(═O)R", —$NR'SO_2R"$, —C(═O)R', —C(═O) OR", —$(CH_2)_q$OR', —OC(═O)R', —$(CR'R")_q OCH_2C_2R'$, —$(CR'R")_q$C(═O)R', —O$(CR'R")_q$C(═O)R', —$C_2(CR'R")_q$O R', —$(CR'R")_q$NR'N", —OC(═O)NR'R" and —NR'C(═O)OR' where R' and R" are individually hydrogen or lower alkyl (e.g., straight chain or branched alkyl including $C_1$–$C_8$, preferably $C_1$–$C_5$, such as methyl, ethyl, or isopropyl), an aromatic group-containing species or a substituted aromatic groupcontaining species, and q is an integer from 1 to 6. R' and R" can form a cycloalkyl functionality. Representative aromatic groups include carbocyclic (phenyl, biphenyl, naphthyl, etc.) and heterocyclic (pyridinyl, pyrinidinyl, quinolinyl, indolyl, etc.) rings.

As employed herein, "alkyl" refers to straight chain or branched alkyl radicals including $C_1$–$C_8$, preferably $C_1$–$C_5$, such as methyl, ethyl, or isopropyl, and cyclic alkyl radicals up to 8 carbonss; "substituted alkyl" refers to alkyl radicals further bearing one or more substituent species such as hydroxy, alkoxy, mercapto, aryl, heterocyclo, halo, amino, carboxyl, carbamyl, cyano, and the like; "alkenyl" refers to straight chain or branched hydrocarbon radicals including $C_1$–$C_8$, preferably $C_1$–$C_5$ and having at least one carbon-carbon double bond; "substituted alkenyl" refers to alkenyl radicals further bearing one Or more substituent species as defined above; "aryl" refers to aromatic radicals having six to ten carbon atoms; "substituted aryl" refers to aryl radicals further bearing one or more substituent species as defined above; "alkylaryl" refers to alkyl-substituted aryl radicals; "substituted alkylaryl" refers to alkylaryl radicals further bearing one or more substituent species as defined above; "arylalkyl"refers to aryl-substituted alkyl radicals; "substituted arylalkyl" refers to arylalkyl radicals further bearing one or more substituent species as defined above; "heterocyclyl" refers to saturated or unsaturated cyclic radicals containing one or more heteroatoms (e.g., O, N, S) as part of the ring structure and having two to seven carbon atoms in the ring; "substituted heterocyclyl" refers to heterocyclyl radicals further bearing one or more substituent species as defined above.

As employed herein, the term "heteroaryl" refers to heterocyclic aromatic radicals, such as pyridinyl, pyrimidinyl, pyrazinyl, pyridazinyl, quinolinyl, furanyl, thienyl, pyrrolyl, indolyl, benzoxazolyl, etc.; "non-aromatic heterocyclyl" refers to heterocyclic radicals, saturated or unsaturated, which are not aromatic, such as tetrahydrofuranyl, tetrahydropyranyl, tetrahydrothienyl, tetrabydrothiopyranyl, pyrrolidinyl, piperidinyl, etc.; "non-aromatic beterocyclylalkyl" refers to nonaromatic heterocyclyl radicals attached through an alkylene chain or up to four carbon atoms; in each case, "substituted" refers to the replacement of one or more of the hydrogens in the group with a non-hydrogen substituent species, as described above.

The preferred embodiments of the invention are those in which one or two of X, X' and X" are nitrogen, the most preferred being the case in which only X" is nitrogen. When only X' is nitrogen, it is preferred that A is attached at the C-5 position of the pyridine ring and that k is 0 or 1.

Cx is preferably:

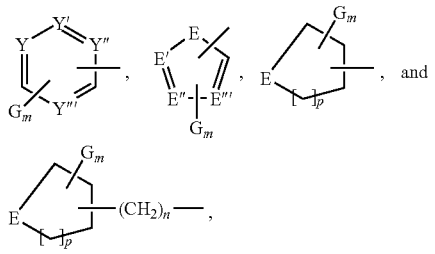

wherein Y, Y', Y" and Y'" are individually nitrogen, nitrogen bonded to oxygen, or carbon bonded to hydrogen or a substituent species, G; E is oxygen, sulfur or nitrogen bonded to hydrogen or a substituent species, G; E', E" and E'" are individually nitrogen or carbon bonded to hydrogen or a substituent species, 0; m is 0, 1, 2, 3 or 4; p is 0, 1, 2 or 3; n is 0, 1, 2, 3 or 4; and 0 is selected fromy the group consisting of alkyl, substituted alkyl, alkenyl, substituted alkenyl, non-aromatic heterocyclyl, substituted non-aromatic heterocyclyl, aryl, substituted aryl, heteroaryl, substituted heterory, alkylaryl, substituted alkylaryl, arylalkyl, substituted arylalkyl, —F, —Cl, —Br, —I, —OR', —NR'R", —$CF_3$, —CN, —$N_3$, —$NO_2$, —$C_2$R', —SR', —SOR', —$SO_2CH_3$, —$SO_2$NR'R", —C(=O)NR'R", —NR'C(=O)R", —NR'$SO_2$R", —C(=O)R', —C(=O)OR', —$(CH_2)_q$OR', —OC(=O)R', —(CR'R")$_q$OCH$_2$C$_2$R', —(CR'R")$_q$C(=O)R', —O(CR'R")$_q$C(=O)R', —C$_2$(CR'R")$_q$O R', —(CR'R")$_q$NR'R", —OC(=O)NR'R" and —NR'C(=O)OR' where R' and R" are individually hydrogen, lower alkyl, an aromatic groupcontaining species or a substituted aromatic groupontaining species, and q is an integer from 1 to 6. Preferably Y, Y', Y", Y'", E', E" and E'" are all carbon bonded to a substituent species. Alternatively one or two of Y, Y', Y", Y'", E', E" and E'" are nitrogen and the remaining are carbon bonded to a substituent species. R' and R" can form a cycloalkyl functionality. Representative aromatic groups include carbocyclic (phenyl, biphenyl, naphthyl, etc.) and heterocyclic (pyridinyl, pyrimidinyl, quinolinyl, indolyl, etc.) rings. Adjacent non-hydrogen substituent species, G, may combine to form one or more saturated or unsaturated, substituted or unsubstituted, carbocyclic or heterocyclic rings containing, but not limited to, ether, acetal, ketal, amine, ketone, lactone, lactam, carbamate and urea functionalities.

Representative compounds of the present invention include the following:

(1S,4S)-2-(5-phenoxy-3-pyridyl)-2,5-diazabicyclo[2.2.1]heptane (1S,4R)-2-(5-phenoxy-3-pyridyl)-2,5-diazabicyclo[2.2.1]heptane (1S,4S)-2-(5-(3-methoxyphenoxy)-3-pyridyl)-2,5-diazabicyclo[2.2.1]heptane (1S,4R)-2-(5-(3-methoxyphenoxy)-3-pyridyl)-2,5-diazabicyclo[2.2.1]heptane (1S,4S)-2-(5-(4-methoxyphenoxy)-3-pyridyl)-2,5-diazabicyclo[2.2.1]heptane (1S,4R)-2-(5-(4-methoxyphenoxy)-3-pyridyl)-2,5-diazabicyclo[2.2.1]heptane (1S,4S)-2-(5-(3,4-dimethoxyphenoxy)-3-pyridyl)-2,5-diazabicyclo[2.2.1]heptane (1S,4R)-2-(5-(3,4-dimethoxyphenoxy)-3-pyridyl)-2,5-diazabicyclo[2.2.1]heptane (1S,4S)-2-(5-(4-fluorophenoxy)-3-pyridyl)-2,5-diazabicyclo[2.2.1]heptane (1S,4R)-2-(5-(4-fluorophenoxy)-3-pyridyl)-2,5-diazabicyclo[2.2.1]heptane (1S,4S)-2-(5-benzoyl-3-pyridyl)-2,5-diazabicyclo[2.2.1]heptane (1S,4R)-2-(5-benzoyl-3-pyridyl)-2,5-diazabicyclo[2.2.1]heptane (1S,4S)-2-(5-(4(N-phenylpiperidinyl)oxy)-3-pyridyl)-2,5-diazabicyclo[2.2.1]heptane (1S,4R)-2-(5-(4-(N-phenylpiperidinyl)oxy)-3-pyridyl)-2,5-diazabicyclo[2.2.1]heptane (1S,4S)-2-(5-(4-(N-trifluoroacetylpiperidinyl)oxy)-3-pyridyl)-2,5-diazabicyclo[2.2.1]heptane (1S,4R)-2-(5-(4-(N-trifluoroacetylpiperidinyl)oxy)-3-pyridyl)-2,5-diazabicyclo[2.2.1]heptane The following compounds also are representative compounds of the present invention:

6-methyl-3-(5-phenyl-3-pyridyl)-3,6-diazabicyclo[3.2.1]octane 6-methyl-3-(5-phenoxy-3-pyridyl)-3,6-diazabicyclo[3.2.1]octane 6-methyl-3-(5-(3-methoxyphenoxy)-3-pyridyl)-3,6-diazabicyclo[3.2.1]octane 6-methyl-3-(5-(4-methoxyphenoxy)-3-pyridyl)-3,6-diazabicyclo[3.2.1]octane 6-methyl-3-(5-(3,4-dimethoxyphenoxy)-3-pyridyl)-3,6-diazabicyclo[3.2.1]octane
6-methyl-3-(5-(4-fluorophenoxy)-3-pyridyl)-3,6-diazabicyclo[3.2.1]octane
6-methyl-3-(5-benzoyl-3-pyridyl)-3,6-diazabicyclo[3.2.1]octane
6-methyl-3-(5-(4-(N-phenylpiperidinyl)oxy)-3-pyridyl)-3,6-diazabicyclo[3.2.1]octane
3-methyl-6-(5-phenyl-3-pyridyl)-3,6-diazabicyclo[3.2.1]octane
3-methyl-6-(5-phenoxy-3-pyridyl)-3,6-diazabicyclo[3.2.1]octane
3-methyl-6-(5-(3-methoxyphenoxy)-3-pyridyl)-3,6-diazabicyclo[3.2.1]octane
3-methyl-6-(5-(4-methoxyphenoxy)-3-pyridyl)-3,6-diazabicyclo[3.2.1]octane
3-methyl-6-(5-(3,4-dimethoxyphenoxy)-3-pyridyl)-3,6-diazabicyclo[3.2.1]octane
3-methyl-6-(5-(4-fluorophenoxy)-3-pyridyl)-3,6-diazabicyclo[3.2.1]octane
3-methyl-6-(5-benzoyl-3-pyridyl)-3,6-diazabicyclo[3.2.1]octane
3-methyl-6-(5-(4-(N-phenylpiperidinyl)oxy)-3-pyridyl)-3,6-diazabicyclo[3.2.1]octane The following compounds also are representative compounds of the present invention:

6-(5-phenyl-3-pyridyl)-3,6-diazabicyclo[3.2.2]nonane
6-5-phenoxy-3-pyridyl)-3,6-diazabicyclo[3.2.2]nonane
6(5-(3-methoxyphenoxy)-3-pyridyl)-3,6-diazabicyclo[3.2.2]nonane
6-(5-(4-methoxyphenoxy)-3-pyridyl)-3,6-diazabicyclo[3.2.2]nonane
6-(5-(3,4-dimethoxyphenoxy)-3-pyridyl)-3,6-diazabicyclo[3.2.2]nonane
6-(5-(4-fluorophenoxy)-3-pyridyl)-3,6-diazabicyclo[3.2.2]nonane
6-(5-benzoyl-3-pyridyl)-3,6-diazabicyclo[3.2.2]nonane
6-(5-(4-phenylpiperidinyl)oxy)-3-pyridyl)-3,6-diazabicyclo[3.2.2]nonane
3-(5-phenyl-3-pyridyl)-3,6-diazabicyclo[3.2.2]nonane
3-(5-phenoxy-3-pyridyl)-3,6-diazabicyclo[3.2.2]nonane
3(5-(3-methoxyphenoxy)-3-pyridyl)-3,6-diazabicyclo[3.2.2]nonane
3-(5-(4-methoxyphenoxy)-3-pyridyl)-3,6-diazabicyclo[3.2.2]nonane
3-(5-(3,4-dimethoxyphenoxy)-3-pyridyl)-3,6-diazabicyclo[3.2.2]nonane
3-(5-(4-fluorophenoxy)-3-pyridyl)-3,6-diazabicyclo[3.2.2]nonane
3-(5-benzoyl-3-pyridyl)-3,6-diazabicyclo[3.2.2]nonane
3-(5-(4-phenylpiperidinyl)oxy)-3-pyridyl)-3,6-diazabicyclo[3.2.2]nonane
3-(5-phenyl-3-pyridyl)-3,7-diazabicyclo[3.3.1]nonane
3-(5-phenoxy-3-pyridyl)-3,7-diazabicyclo[3.3.1]nonane
3(5-(3-methoxyphenoxy)-3-pyridyl)-3,7-diazabicyclo[3.3.1]nonane
3-(5-(4-methoxyphenoxy)-3-pyridyl)-3,7-diazabicyclo[3.3.1]nonane
3-(5-(3,4-dimethoxyphenoxy)-3-pyridyl)-3,7-diazabicyclo[3.3.1]nonane
3-(5-(4-fluorophenoxy)-3-pyridyl)-3,7-diazabicyclo[3.3.1]nonane
3-(5-benzoyl-3-pyridyl)-3,7-diazabicyclo[3.3.1]nonane
3-(5-(4-phenylpiperidinyl)oxy)-3-pyridyl)-3,7-diazabicyclo[3.3.1]nonane The manner in which N-aryl diazabicyclic compounds of the present invention are synthetically produced can vary. Commercially available (Aldrich Chemical) (1S,4S)-N-(tert-butoxycarbonyl)-2,5-diazabicyclo[2.2.1]heptane can be coupled with a variety of aromatic halides and heteroaromatic halides using palladium catalysis. See Yang et al., J. Organomet Chem. 576:125 (1999), Wolfe et al., Acc. Chem. Res. 31:805 (1998) and Hartwig et al., J. Org. Chem. 64: 5575 (1999). For example, treatment of 3,5-dibromopyridine with (1S,4S)-N-(tert-butoxycarbonyl)-2,5-diazabicyclo[2.2.1]heptane in the presence of sodium tert-butoxide and a catalytic amount of tris (dibenzylideneacetone)dipalladium(0) and rac-2,2'-bis (diphenylphosphino)-1,1'-binaphthyl in toluene provides (1S,4S)-5-(tert-butoxycarbonyl)-2-(5-bromo-3-pyridyl)-2,5-diazabicyclo[2.2.1]heptane. The N-tert-butoxycarbonyl protecting group is readily removed in the presence of acid to provide (1S,4S)-2-(5-bromo-3-pyridyl)-2,5-diazabicyclo [2.2.1]heptane. Use of the other enantiomer, (1R,4R)-N-(tert-butoxycarbonyl)-2,5-diazabicyclo[2.2.1]heptane, in the palladium-catalyzed coupling will lead to (1R,4R)-2-(5-bromo-3-pyridyl)-2,5-diazabicyclo[2.2.1]heptane. Both the (1S,4S) and the (1R,4R) enantiomers of the N-(tert-butoxycarbonyl)-2,5-diazabicyclo[2.2.1]heptane can be synthesized from hydroxyproline isomers as described in U.S. Pat. Nos. 5,095,121 and 5,196,548 to Braish and Fox and by Braish and Fox in in J. Org. Chem. 55:1694 (1990). Also reported in these references are the syntheses of the N-benzyl derivatives of (1S,4S)- and (1R,4R)-2,5-diazabicyclo[2.2.1]heptane. Coupling of these diazabicycles with 3,5-dibromopyridine, as described above, would generate the corresponding enantiomeric 5-benzyl-2-(5-bromo-3-pyridyl)-2,5-diazabicyclo[2.2.1]heptanes. Likewise, coupling with 3-bromopyridine would produce the enantiomeric 5-benzyl-2-(3-pyridyl)-2,5-diazabicyclo[2.2.1]heptanes. The coupling reactions described here tolerate considerable substituent functionality, thus providing a means of synthesizing a wide variety of N-benzyl- or N-tert-butoxycarbonyl-protected 2-(3-pyridyl)-2,5-diazabicyclo[2.2.1]heptanes with subtituents on the pyridine ring.

A suitably protected derivative of either 2-(5-bromo-3-pyridyl)-2,5-diazabicyclo[2.2.1]heptane enantiomer can be elaborated to give a number of compounds possessing substituents at the C-5 position of the pyridine. For example, 5-benzyl-2-(5-bromo-3-pyridyl)-2,5-diazabicyclo[2.2.1] heptane can be converted into the corresponding 5-amino-substituted compound by the general method of Zwart et al., Recueil Trav. Chim. Pays-Bas 74:1062 (1955), in which the bromo-substituted compound is heated with aqueous ammonia in the presence of a copper catalyst. 5-Alkylamino-substituted compounds can be prepared in a similar manner. 5-Ethynyl-substituted compounds can be prepared from the 5-bromo-substituted compound by palladium-catalyzed coupling using 2-methyl-3-butyn-2-ol, followed by base-catalyzed (sodium hydride) removal of the acetone unit, according to the general techniques described in Cosford et al., J. Med. Chem. 39:3235 (1996). The 5-ethynyl analogs can be converted into the corresponding 5ethenyl and subsequently to the corresponding 5-ethyl analogs by successive catalytic hydrogenation reactions (which would also remove the benzyl protecting group from the diazabicycle). The 5-azido-substituted analogs can be prepared from the 5-bromo-substituted compound by reaction with lithium azide in N,N-dimethylformamide. 5-Alkylthio-substituted analogs can be prepared from the 5-bromo-substituted compound by reaction with an appropriate sodium alkylmercaptide (sodium alkanethiolate), using techniques known to those skilled in the art of organic synthesis.

A number of other analogs, bearing substituents in the 5 position of the pyridine ring, can be synthesized from 5-benzyl-2-(5-amino-3-pyridyl)-2,5-diazabicyclo[2.2.1] heptane (the synthesis of which is described above) via the 5-diazonium salt intermediate. Either enantiomer of the 5-amino compound may be utilized. Among the other 5-substituted analogs that can be produced from 5-diazonium salt intermediates are: 5-hydroxy analogs, 5-alkoxy analogs, 5-fluoro analogs, 5-chloro analogs, 5-bromo analogs, 5-iodo analogs, 5-cyano analogs, and 5-mercapto analogs. These compounds can be synthesized using the general techniques set forth in Zwart et al., supra. For example, 5-hydroxy-substituted analogs can be prepared from the reaction of the corresponding 5-diazonium salt intermediates with water. 5-Alkoxy analogs can be made from the reaction of the diazonium salts with alcohols. 5-Fluoro-substituted analogs can be prepared from the reaction of the 5-diazonium salt intermediates with fluoroboric acid. 5-Chloro-substituted analogs can be prepared from the reaction of the 5-amino compounds with sodium nitrite and hydrochloric acid in the presence of copper chloride. 5-Cyano-substituted analogs can be prepared from the reaction of the corresponding 5-diazonium salt intermediates with potassium copper cyanide. Appropriate 5-diazonium salt intermediates can also be used for the synthesis of mercapto-substituted analogs using the general techniques described in Hoffman et al., J. Med. Chem. 36:953 (1993). The 5-mercapto-substituted analogs can in turn be converted to the 5-alkylthio-substituted analogs by reaction with sodium hydride and an appropriate alkyl bromide. 5-Acylamido analogs of the aforementioned compounds can be prepared by reaction of the corresponding 5-amino compounds with an appropriate acid anhydride or acid chloride using techniques known to those skilled in the art of organic synthesis.

5-Hydroxy-substituted analogs of the aforementioned compounds can be used to prepare corresponding 5-alkanoyloxy-substituted compounds by reaction with the appropriate acid, acid chloride, or acid anhydride. Likewise, the 5-hydroxy compounds are precursors of both the 5-aryloxy and 5-heteroaryloxy via nucleophilic aromatic substitution at electron deficient aromatic rings (e.g., 4-fluorobenzonitrile and 2,4-dichloropyrimidine). Such chemistry is well known to those skilled in the art of organic synthesis. Non-aromatic heterocyclyloxy derivatives can also be prepared from the 5-hydroxy compounds via Mitsunobu chemistry, in which a trialkyl- or triarylphosphine and diethyl azodicarboxylate are typically used. See Hughes, Org. React (N.Y.) 42: 335 (1992) and Hughes, Org. Prep. Proced. Int. 28: 127 (1996). Thus, various N-substituted-4-hydroxypiperidines can be coupled with the 5-hydroxypyridine compounds to give compounds bearing N-substituted piperidinyloxy substituents in the 5 position of the pyridine ring.

5-Cyano-substituted analogs of the aforementioned compounds can be hydrolyzed to afford the corresponding 5-carboxamido-substituted compounds. Further hydrolysis results in formation of the corresponding 5-carboxylic acid-substituted analogs. Reduction of the 5-cyano-substituted analogs with lithium aluminum hydride yields the corresponding 5-aminomethyl analogs. 5-Acyl-substituted analogs can be prepared from corresponding 5-carboxylic acid-substituted analogs by reaction with an appropriate alkyllithium using techniques known to those skilled in the art of organic synthesis.

5-Carboxylic acid-substituted analogs of the aforementioned compounds can be converted to the corresponding esters by reaction with an appropriate alcohol and acid catalyst. Compounds with an ester group at the 5-pyridyl position can be reduced with sodium borohydride or lithium aluminum hydride to produce the corresponding 5-hydroxymethyl-substituted analogs. These analogs, in turn, can be converted to compounds bearing an ether moiety at the 5-pyridyl position by reaction with sodium hydride and an appropriate alkyl halide, using conventional techniques. Alternatively, the 5-hydroxymethyl-substituted analogs can be reacted with tosyl chloride to provide the corresponding 5-tosyloxymethyl analogs. The Scarboxylic acid-substituted analogs can also be converted to the corresponding 5-alkylaminoacyl analogs by reaction with an appropriate alkylamine and thionyl chloride. Certain of these amides are known to readily undergo nucleophilic acyl substitution to produce ketones. Thus, the so-called Weinreb amides (N-methoxy-N-methylamides) react with aryllithium reagents to produce the corresponding diaryl ketones. For example, see Selnick et al., Tet. Lett. 34: 2043 (1993).

5-Tosyloxymethyl-substituted analogs of the aforementioned compounds can be converted to the corresponding 5-methyl-substituted compounds by reduction with lithium aluminum hydride. 5--Tosyloxymethyl-substituted analogs of the aforementioned compounds can also be used to produce 5-alkyl-substituted compounds via reaction with an alkyllithium. 5-Hydroxy-substituted analogs of the aforementioned compounds can be used to prepare 5—N-alkylcarbamoyloxy-substituted compounds by reaction with N-alkylisocyanates. 5-Amino-substituted analogs of the aforementioned compounds can be used to prepare 5-Nalkoxycarboxamido-substituted compounds by reaction with alkyl chlorofornate esters, using techniques known to those skilled in the art of organic synthesis.

Chemistries analogous to those described hereinbefore for the preparation of 5-substituted (pyridine) analogs of diazabicyclic compounds can be devised for the synthesis of analogs bearing substituents in the 2, 4, and 6 positions of the pyridine ring. For example, a number of 2-, 4-, and 6-aminopyridyl diazabicyclic compounds can be converted to the corresponding diazonium salt intermediates, which can be transformed to a variety of compounds with substituents at the 2, 4, and 6 positions of the pyridine ring as was described for the 5-substituted analogs above. The requisite 2-, 4-, and 6-aminopyridyl diazabicycles are available via the Chichibabin reaction of unsubstituted pyridyl diazabicycles (e.g., 5-benzyl-2-(3-pyridyll)-2,5-diazabicyclo[2.2.1] heptane, described previously). Similar reactions are described in Chemistry of Heterocyclic Compounds, Volume 14, part 3, pp.3–5 (Interscience Publishers, 1962) and by Lahti et al., J. Med. Chem. 42:2227 (1999). After the desired pyridine ring functional group manipulation has been accomplished, the benzyl protecting group can be removed from the diazabicycle using hydrogenation conditions.

In an alternative approach to the synthesis of pyridine-substituted pyridyl diazabicyclic compounds, 3,5-dibromopyridine can be converted into the corresponding 3-bromo-5-alkoxy- and 3-bromo-5-arylopyridines by the action of sodium alkoxides or sodium aryloxides. Procedures such as those described by Comins et al., J. Org. Chem. 55: 69 (1990) and Hertog et al., Recueil Trav. Chim. Pays-Bas 74: 1171 (1955) are used. This is exemplified by the preparation 2-(5-(4-methoxyphenoxy)-3-pyridyl)-2,5-diazabicyclo[2.2.1]heptane. Reaction of 3,5-dibromopyridine with sodium 4-methoxyphenoxide in N,N-dimethylformamide gives 3-bromo-5-(4-methoxyphenoxy) pyridine. Coupling of 3-bromo-5-(4-methoxyphenoxy) pyridine with (1S,4S)-N-(tert-butoxycarbonyl)-2,5-diazbicyclo

[2.2.1]heptane in the presence of sodium tert-butoxide and a catalytic amount of tris (dibenzylideneacetone)dipalladium (0) and 2,2'-bis (diphenylphosphino)-1,1'-binaphthyl in toluene provides (1S,4S)-2-(5-(4-methoxyphenoxy)-3-pyridyl)-5-(tert-butoxycarbonyl)-2,5-diazabicyclo[2.2.1]heptane. Removal of the N-tert-butoxycarbonyl group, using trifluoroacetic acid, produces (1S,4S)-2-(5-(4-methoxyphenoxy)-3-pyridyl)-2,5-diazabicyclo[2.2.1]heptane.

Compounds of the present invention can also be produced using 5-bromonicotinic acid as a precursor. Thus, the acid can be converted to the acyl chloride (using thionyl chloride) and subsequently used in Friedel-Crafts-type acylations, producing 3-bromo-5-(arylcarbonyl)pyridines, which then serve as substrates for the palladium-catalyzed coupling reaction described earlier. See, for example, Villani and King. Org. Syn. Coll. Vol. 4: 88 (1963).

Other aryl halides undergo the palladium-catalyzed coupling reaction described previously. Thus, (1S,4S)-2-(5-pyrimidinyl)-2,5-diazabicyclo[2.2.1]heptane is prepared in a similar manner from 5-bromopyrimidine and (1S,4S)-N-(tert-butoxycarbonyl)-2,5-diazabicyclo[2.2.1]heptane, followed by deprotection of the resulting intermediate. (1S,4S)-2-(6-Chloro-3-pyridazinyl)-2,5-diazabicyclo[2.2.1]heptane is synthesized similarly from 3,6-dichloropyridazine and (1S,4S)-N-(tert-butoxycarbonyl)-2,5-diazabicyclo[2.2.1] heptane, followed by deprotection of the resulting intermediate. This technology is especially applicable in cases (like 3-bromopyridine, 3,5-dibromopyridine, and 5-bromopyrimidine) where the aromatic ring is not activated toward nucleophilic aromatic substitution.

The present invention also relates to the use of other diazabicyclic systems in palladiumcatalyzed coupling reactions with aryl halides. The procedures described by Old et al., J. Am. Chem. Soc. 120:9722 (1998) and Hartwig et al., J. Org. Chem. 64:5575 (1999) are typical of the conditions used for the coupling. For example, coupling of 3-bromopyridine with 6-carboethoxy-3,6-diazabicyclo [3.2.2]nonane under palladium catalysis will provide 3-(3-pyridyl)-6-carboethoxy-3,6-diazabicyclo[3.2.2]nonane. Hydrolysis of the carboethoxy protecting group using sodium hydroxide/ethylene glycol/water or HBr in acetic acid will lead to 3-(3-pyridyl)-3,6-diazabicyclo[3.2.2]nonane. 6-Carboethoxy-3,6-diazabicyclo[3.2.2]nonane can be produced from 3-benzyl-6-carboethoxy-3,6-diazabicyclo [3.2.2]nonane by hydrogenation in the presence of palladium on carbon. The synthesis of the requisite 3-benzyt-6-carboethoxy-3,6-diazabicyclo[3.2.2]nonane is described by Fray et al., J. Org. Chem. 53:896 (1988) and in European Patent Application No. 88305925.5, filed Jun. 28, 1988 (Publication No. 0297858A2). Other appropriately substituted aryl halides (e.g., 3,5-dibromopyridine and 5-bromopyrirdine) can be coupled similarly and subsequently transformed into 3-aryl-3,6-diazabicyclo[3.2.2]nonanes.

The 3,6-diazabicyclo[3.2.2]nonane ring system can also be coupled to aryl halides via the 6-aza position, producing 6-aryl-3,6-diazabicyclo-[3.2.2]nonanes, which are isomeric to the 3-aryl-3,6-diazabicyclo[3.2.2]no- nanes described previously. Thus, the aforementioned 3-benzyl-6-carboethoxy-3,6-diazabicyclo[3.2.2]nonane can be hydrolyzed to 3-benzyl-3,6-diazabicyclo[3.2.2]nonane, which can subsequently be coupled to an aryl halide in a palladium-catalyzed reaction. The 6-aryl-3-benzyl-3,6-diazabicyclo [3.2.2]nonane product can then be hydrogenated to give a 6-aryl-3,6-diazabicyclo[3.2.2]nonane.

Another example of a diazabicyclic analog, which can be incorporated into compounds of the present invention, is 3,6-diazabicyclo[3.2.1]octane. For instance, the synthesis of both 3-methyl-3,6-diazabicyclo[3.2.1]octane and 6-methyl-3,6-diazabicyclo[3.2.1]octane is described in European Patent Application No. 88305925.5, filed Jun. 28, 1988 (Publication No. 0297858A2). Either of these amines can be coupled with 3-bromopyridine, in a palladium-catalyzed process, to give isomeric products 3-methyl-6-(3-pyridyl)-3,6-diazabicyclo[3.2.1]octane and 6-methyl-3-(3-pyridyl)-3,6-diazabicyclo[3.2.1]octane. The use of other appropriately substituted aryl halides in the coupling reaction will lead to other N-aryl 3,6-diazabicyclo[3.2.1]octane products.

Yet another diazabicycle that is illustrative of the present invention is the 3,7-diazabicyclo[3.3.1]nonane ring system. Thus 3,7-dibenzyl-3,7-diazabicyclo[3.3.1]nonan-9-one, which is readily prepared by a double Mannich reaction of N-benzyl-4-piperidone with formaldehyde and benzylamine (see Garrison et al., J. Org. Chem. 58: 7670 (1993)), can be converted into 3,7-dibenzyl-3,7-diazabicyclo[3.3.1]nonane by either of several deoxygenation reactions. For instance, a Wolff-Kishner reduction, using procedures similar to those described by Berlin et al., Org. Prep. and Proc. Int. 31:413 (1999) or the tosylhydrazone method described by Caglioti Org. Syn. Coll. Vol. 6:62 (1988), will convert the ketone into the corresponding alkane. Then removal of the benzyl group can be accomplished by hydrogenation over palladium on carbon. The hydrogenation product of 3,7-diazabicyclo [3.3.1]nonane can be coupled directly with an aryl halide (such as 3-bromopyridine) under conditions in which the diazabicycle is used in excess to minimize the production of 3,7-diaryl-3,7-diazabicyclo[3.3.1]nonane. Alternatively, reacting an excess of the 3,7-diazabicyclo[3.3.1]nonane with di-tert-butyl-dicarbonate will provide the mono-protected diazabicycle, 3-(tert-butoxycarbonyl)-3,7-diazabicyclo [3.3.1]nonane, which subsequently can be coupled (palladium catalysis) and deprotected (trifluoroacetic acid) as described previously.

The present invention relates to a method for providing prevention of a condition or disorder to a subject susceptible to such a condition or disorder, and for providing treatment to a subject suffering therefrom. For example, the method comprises administering to a patient an amount of a compound effective for providing some degree of prevention of the progression of a CNS disorder (i.e., provide protective effects), amelioration of the symptoms of a CNS disorder, and amelioration of the recurrence of a CNS disorder. The method involves administering an effective amount of a compound selected from the general formulae, which are set forth hereinbefore. The present invention relates to a pharmaceutical composition incorporating a compound selected from the general formulae, which are set forth hereinbefore. Optically active compounds can be employed as racemic mixtures or as pure enantiomers. The compounds can be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, galactarate, propionate, succinate, lactate, glycolate, malate, tartrate, citrate, maleate, flimarate, methanesulfonate, p-toluenesulfonate, and ascorbate; salts with an acidic amino acid such as aspartate and glutamate; alkali metal salts such as sodium and potassium; alkaline earth metal salts such as magnesium and calcium; ammonium salt; organic basic salts such as trimethylamine, triethylamine, pyridine, picoline, dicyclohexylamine, and N,N'-dibenzylethylenediamine; and salts with a basic amino acid such as lysine and arginine. The salts may be in some cases hydrates or ethanol solvates. Representative salts are provided as described in U.S. Pat. No. 5,597,919 to Dull et al., U.S. Pat. No. 5,616,716 to Dull et al. and U.S. Pat. No. 5,663,356 to Ruecroft et al., the disclosures of which are incorporated herein by reference in their entirety.

Compounds of the present invention are useful for treating those types of conditions and disorders for which other types of nicotinic compounds have been proposed as therapeutics. See, for example, Williams et al., Drug News Perspec. 7(4):205 (1994), Arneric et al., CNS Drug Rev. 1(1):1 (1995), Arneric et al., Exp. Opin. Invest. Drugs 5(1):79 (1996), Bencherif et al., J. Pharmacol. Exp. Ther. 279:1413 (1996), Lippiello et al., J. Pharmacol. Exp. Ter. 279:1422 (1996), Damaj et al., J. Pharmacol. Exp. Ther. 291:390 (1999); Chiari et al., Anesthesiology 91:1447 (1999); Lavand'homme and Eisenbach, Anesthesiology 91:1455 (1999); Holladay et al., J. Med Chem. 40(28):4169 (1997), Bannon et al., Science 279:77 (1998), PCT WO 94/08992, PCT WO 96/31475, and U.S. Pat. No. 5,583,140 to Bencherif et al., U.S. Pat. No. 5,597,919 to Dull et al., and U.S. Pat. No. 5,604,231 to Smith et al., the disclosures of which are incorporated herein by reference in their entirety. Compounds of the present invention can be used as analgesics, to treat ulcerative colitis, inflammatory and autoimmune diseases (e.g., arthritis, cholangitis, stomatitis, pouchitis, viral pneumonitis), to treat a variety of neurodegenerative diseases, and to treat convulsions such as those that are symptomatic of epilepsy. CNS disorders which can be treated in accordance with the present invention include pre-senile dementia (early onset Alzheimer's disease), senile dementia (dementia of the Alzheimer's type), HIV-dementia, multiple cerebral infarcts, Parkinsonism including Parkison's disease, Pick's disease, Huntington's chorea, tardive dyskinesia, hyperkinesia, mania, attention deficit disorder, anxiety, depression, mild cognitive impairment, dyslexia, schizophrenia and Tourette's syndrome. Compounds of the present invention also can be used to treat conditions such as syphillis and Creutzfeld-Jakob disease. The compounds of the present invention also can be appropriately synthesized and used as or within pharmaceutical compositions that are used as diagnostic probes.

The pharmaceutical composition also can include various other components as additives or adjuncts. Exemplary pharmaceutically acceptable components or adjuncts which are employed in relevant circumstances include antioxidants, free-radical scavenging agents, peptides, growth factors, antibiotics, bacteriostatic agents, immunosuppressives, anticoagulants, buffering agents, anti-inflammatory agents, anti-pyretics, time-release binders, anaesthetics, steroids, vitamins, minerals and corticosteroids. Such components can provide additional therapeutic benefit, act to affect the therapeutic action of the pharmaceutical composition, or act towards preventing any potential side effects which may be imposed as a result of administration of the pharmaceutical composition. In certain circumstances, a compound of the present invention can be employed as part of a pharmaceutical composition with other compounds intended to prevent or treat a particular disorder.

The manner in which the compounds are administered can vary. The compounds can be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); orally (e.g., in liquid form within a solvent such as an aqueous or non-aqueous liquid, or within a solid carrier); intravenously (e.g., within a dextrose or saline solution); as an infuision or injection (e.g., as a suspension or as an emulsion in a pharmaceutically acceptable liquid or mixture of liquids); intrathecally; intracerebroventricularly; or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time-release capsule. As another example, the compounds can be delivered tansdermally using the types of patch technologies available from Novartis and Alza Corporation. The administration of the pharmaceutical compositions of the present invention can be intermittent or at a gradual, continuous, constant or controlled rate to a warm-blooded animal (e.g., a mammal such as a mouse, rat, cat, rabbit, dog, pig, cow, or monkey), but advantageously is administered preferably to a human being. In addition, the time of day and the number of times per day that the pharmaceutical formulation is administered can vary. Preferable administration is such that the active ingredients of the pharmaceutical formulation interact with receptor sites within the body of the subject that affect the functioning of the CNS. More specifically, in treating a CNS disorder, preferable administration is designed to optimize the effect upon those relevant receptor subtypes that have an effect upon the functioning of the CNS, while minimizing the effects upon muscletype receptor subtypes. Other suitable methods for administering the compounds of the present invention are described in U.S. Pat. No. 5,604,231 to Smith et al.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. Thus, when treating a CNS disorder, an effective amount of compound is an amount sufficient to pass across the blood-brain barrier of the subject, to bind to relevant receptor sites in the brain of the subject and to activate relevant nicotinic receptor subtypes (e.g., provide neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the recurrence of the symptoms of the disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to activate relevant receptors to effect neurotannsrnitter (e.g., dopamine) release, but the amount should be insufficient to induce effects on skeletal muscles and ganglia to any significant degree. The effective dose of compounds will of course differ from patient to patient, but in general includes amounts starting where CNS effects or other desired therapeutic effects occur but below the amount where muscular effects are observed.

The compounds useful according to the method of the present invention have the ability to pass across the blood-brain barrier of the patient. As such, these compounds have the ability to enter the central nervous system of the patient. The log P values of typical compounds, which are useful in carrying out the present invention, are generally greater than about −0.5, often are greater than about 0, and frequently are greater than about 0.5. The log P values of such typical compounds generally are less than about 3, often are less than about 2, and frequently are less than about 1. Log P values provide a measure of the ability of a compound to pass across a diffusion barrier, such as a biological membrane, including the blood brain barrier. See, for example, Hansch et al., J. Med. Chem.11:1 (1968).

The compounds useful according to the method of the present invention have the ability to bind to, and in most circumstances, cause activation of, nicotinic dopaminergic receptors of the brain of the patient. As such, these compounds have the ability to express nicotinic pharmacology and, in particular, to act as nicotinic agonists. The receptor binding constants of typical compounds useful in carrying out the present invention generally exceed about 0.1 nM, often exceed about 1 nM, and frequently exceed about 10 nM. The receptor binding constants of certain compounds are less than about 100 μM, often are less than about 10 μM and frequently are less than about 5 μM; and of preferred compounds generally are less than about 2.5 μM, sometimes are less than about 1 μM, and can be less than about 100 nM. Receptor binding constants provide a measure of the ability of the compound to bind to half of the relevant receptor sites of certain brain cells of the patient. See, for example, Cheng et al., Biochem. Pharmacol. 22:3099 (1973).

The compounds useful according to the method of the present invention have the ability to demonstrate a nicotinic function by effectively activating neurotransmitter secretion from nerve ending preparations (i.e.,synaptosomes). As such, these compounds have the ability to activate relevant neurons to release or secrete acetylcholine, dopamine, and other neurotransmitters. Generally, typical compounds useful in carrying out the present invention provide for the activation of dopamine secretion in amounts of at least one third, typically at least about 10 times less, frequently at least about 100 times less, and sometimes at least about 1,000 times less than those required for activation of muscle-type nicotinic receptors. Certain compounds of the present invention can provide secretion of dopamine in an amount which is comparable to that elicited by an equal molar amount of (S)-(−)-nicotine.

The compounds of the present invention, when employed in effective amounts in accordance with the method of the present invention, are selective to certain relevant nicotinic receptors, but do not cause significant activation of receptors associated with undesirable side effects at concentrations at least greater than those required for activation of dopamine release. By this is meant that a particular dose of compound resulting in prevention and/or treatment of a CNS disorder is essentially ineffective in eliciting activation of certain ganglionic-type nicotinic receptors at concentration higher than 5 times, preferably higher than 100 times, and more preferably higher than 1,000 times than those required for activation of doparnine release. This selectivity of certain compounds of the present invention against those ganglionic-type receptors responsible for cardiovascular side effects is demonstrated by a lack of the ability of those compounds to activate nicotinic function of adrenal chromaffin tissue at concentrations greater than those required for activation of dopamine release.

Compounds of the present invention, when employed in effective amounts in accordance with the method of the present invention, are effective towards providing some degree of prevention of the progression of CNS disorders, amelioration of the symptoms of CNS disorders, and amelioration to some degree of the recurrence of CNS disorders. However, such effective amounts of those compounds are not sufficient to elicit any appreciable side effects, as demonstrated by increased effects relating to skeletal muscle. As such, administration of certain compounds of the present invention provides a therapeutic window in which treatment of certain CNS disorders is provided and certain side effects are avoided. That is, an effective dose of a compound of the present invention is sufficient to provide the desired effects upon the CNS but is insufficient (i.e., is not at a high enough level) to provide undesirable side effects. Preferably, effective administration of a compound of the present invention resulting in treatment of CNS disorders occurs upon administration of less than ⅕, and often less than 1/10, that amount sufficient to cause certain side effects to any significant degree.

The pharmaceutical compositions of the present invention can be employed to prevent or treat certain other conditions, diseases and disorders. Exemplary of such diseases and disorders include inflammatory bowel disease, pouchitis, acute cholangitis, aphthous stomatitis, arthritis (e.g., rheumatoid arthritis and osteoarthritis), neurodegenerative diseases, cachexia secondary to infection (e.g., as occurs in AIDS, AIDS-related complex and neoplasia), as well as those indications set forth in PCT WO 98/25619. The pharmaceutical compositions of the present invention can be employed in order to ameliorate many of the symptoms associated with those conditions, diseases and disorders. Thus, pharmaceutical compositions of the present invention can be used in treating genetic diseases and disorders, in treating autoimmune disorders such as lupus, as anti-infectious agents (e.g., for treating bacterial, fingal and viral infections, as well as the effects, such as sepsis, of other types of toxins), as anti-inflammatory agents (e.g., for treating acute cholangitis, aphthous stomatitis, asthma, and ulcerative colitis), and as inhibitors of cytokine release (e.g., as is desirable in the treatment of cachexia, inflammation, neurodegenerative diseases, viral infection, and neoplasia). The compounds of the present invention can also be used as adjunct therapy in combination with existing therapies in the management of the aforementioned types of diseases and disorders. In such situations, preferable administration is such that the active ingredients of the pharmaceutical formulation act to optimize effects upon abnormal cytokine production, while minimizing effects upon receptor subtypes such as those that are associated with muscle and ganglia Preferable administration is such that active ingredients interact with regions where cytokine production is affected or occurs. For the treatment of such conditions or disorders, compounds of the present invention are very potent (i.e., affect cytokine production and/or secretion at very low concentrations) and are very efficacious (i.e., significantly inhibit cytokine production and/or secretion to a relatively high degree).

Most preferably, effective doses are at very low concentrations, where maximal effects are observed to occur. Concentrations, determined as the amount of compound per volume of relevant tissue, typically provide a measure of the degree to which that compound affects cytokine production. Typically, the effective dose of such compounds generally requires administering the compound in an amount of less than 5 mg/kg of patient weight. Often, the compounds of the present invention are administered in an amount from less than about 1 mg/kg patent weight and usually less than about 100 μg/kg of patient weight, but frequently between about 10 μg to less than 100 μg/kg of patient weight. For compounds of the present invention that do not induce effects on muscle-type nicotinic receptors at low concentrations, the effective dose is less than 5 mg/kg of patient weight; often such compounds are administered in an amount from 50 μg to less than 5 mg/kg of patient weight. The foregoing effective doses typically represent that amount administered as a single dose, or as one or more doses administered over a 24-hour period.

For human patients, the effective dose of typical compounds generally requires administering the compound in an amount of at least about 1, often at least about 10, and frequently at least about 25 μg/24 hr/patient. For human patients, the effective dose of typical compounds requires administering the compound which generally does not exceed about 500, often does not exceed about 400, and frequently does not exceed about 300 μg/24 hr/patient. In addition, administration of the effective dose is such that the concentration of the compound within the plasma of the patient normally does not exceed 500 μg/mL, often does not exceed 300 pg/mL, and frequently does not exceed 100 pg/mL. When employed in such a manner, compounds of the present invention are dose dependent, and, as such, cause inhibition of cytokine production and/or secretion when employed at low concentrations but do not exhibit those inhibiting effects at higher concentrations. Compounds of the present invention exhibit inhibitory effects upon cytokine production and/or secretion when employed in amounts less than those amounts necessary to elicit activation of relevant nicotinic receptor subtypes to any significant degree.

The following examples are provided to illustrate the present invention and should not be construed as limiting the scope thereof. In these examples, all parts and percentages are by weight, unless otherwise noted. Reaction yields are reported in mole percentages.

EXAMPLES

Assays

Determination of Binding to Relevant Receptor Sites

Binding of the compounds to relevant receptor sites was determined in accordance with the techniques described in U.S. Pat. No. 5,597,919 to Dull et al. Inhibition constants ($K_i$ values), reported in nM, were calculated from the $IC_{50}$ values using the method of Cheng et al., Biochem. Pharmacol. 22:3099 (1973).

Example 1

Sample No. 1 is (1S,4S)-2-(5-(4-methoxyphenoxy)-3-pyridyl)-2,5-diazabicyclo[2.2.1]heptane hernigalactarate, which was prepared in accordance with the following techniques:

3-Bromo-5-(4-methoxyphenoxy)pyridine

To a stirred suspension of sodium hydride (3.0 g of 80% in mineral oil, 100 mmol) in DMF (95 mL) in an ice water bath, 4-methoxyphenol (12.2 g, 96 mmol) was added slowly under a nitrogen atmosphere. The resulting mixture was warmed to ambient temperature and stirred for 1 h. 3,5-Dibromopyridine (15.6 g of 98%, 65 mmol) was added and the mixture was then heated at 85° C. (bath temperature) for 32 h. The mixture was cooled, diluted with water (120 mL), poured into 5N sodium hydroxide (15 mL), and extracted with ether (3×150 mL). The combined ether extracts were dried ($Na_2SO_4$), filtered and concentrated by rotary evaporation, to give a light-yellow oil (21.9 g). The oil was diluted with ethanol and rotary evaporated (twice) to remove residual DMF and then diluted with ether (50 mL) and suction filtered to remove un-reacted 3,5-dibromopyridine. Rotary evaporation and high vacuum treatment left a lard-like product weighing 12.8 g. The product was 94% pure by GC-MS analysis (66% yield) and was sometimes used, without further purification, in subsequent reactions. When desired, further purification (to 99.4%) was accomplished by column chromatography on silica gel, using 85:5:5:4.5:0.5 hexane/chloroform/ethyl acetate/methanol/aqueous ammonia as eluent.

(1S,4S)-2-(5-(4-Methoxyphenoxy)-3-pyridyl)-5-(tert-butoxycarbonyl-2,5-diazabicyclo[2.2.1]heptane In a sealed pressure tube under an argon atmosphere, 3-bromo-5-(4-methoxyphenoxy)pyridine (0.37 g of 94%, 1.2 mmol), (1S,4S)-N-(tert-butoxycarbonyl)-2,5-diazabicyclo[2.2.1]heptane (0.21 g, 1.1 mmol), tris (dibenzylideneacetone)dipalladium(0) (0.02 g, 0.02 mmol, rac-2,2'-bis(diphenylphosphino)-1,1'-binaphthyl (0.025 g, 0.04 mmol), sodium tert-butoxide (0.20 g, 2.0 mmol) and toluene (12 mL) were stirred at 80° C. for 24 h. The reaction mixture was poured into saturated aqueous sodium chloride solution (20 mL) and extracted with diethyl ether (3×30 mL). The combined diethyl ether extracts were washed with saturated aqueous sodium chloride solution (20 mL), dried ($Na_2SO_4$), filtered and concentrated to a brown oil (0.37 g). The material was used without further purification.

(1S,4S)-2-(5-(4-Methoxyphenoxy)-3-pyridyl)-2,5-diazabicyclo[2.2.1]heptane

To a stirred solution of unpurified (1S,4S)-2-(5-(4-methoxyphenoxy)-3-pyridyl)-5-tert-butoxycarbonyl)-2,5-diazabicyclo[2.2.1]heptane (0.37 g) in anisole (3.0 mL) at 0–5° C. under a nitrogen atmosphere, trifluoroacetic acid (2.0 mL) was added dropwise over a 10 min. period. After 0.5 h at 0–5° C. the solution was adjusted to pH 5 using 10% NaOH, followed by extraction with diethyl ether (1×10 mL) to remove the anisole. The aqueous portion was adjusted to pH 11 using 10% NaOH, followed by extraction with diethyl ether (3×25 mL). The combined diethyl ether extracts were dried ($Na_2SO_4$), filtered and concentrated under vacuum to give a yellow oil (0.26 g). The material was used without further purification.

(1S,4S)-2-(5-(4-Methoxyphenoxy)-3-pyridyly-2,5-diazabicyclo[2.2.1]heptane hemigalactarate A solution of unpurified (1S,4S)-2-(5-(4-methoxyphenoxy)-3-pyridyl)-2,5-diazabicyclo[2.2.1] heptane (0.26 g) in ethanol (2 mL) and water (2 mL) was heated at 60° C. as mucic acid (0.075 g, 0.36 mmol) was added. The mixture was heated for 30 min then filtered through glass wool and concentrated to approximately 1 mL. The solution was treated with diethyl ether (4 mL). The resulting precipitate was collected, washed with diethyl ether (1 mL) and dried at 45° C. for 4 h to afford 0.195 g (44% overall for three steps) of white solid, mp 172–182° C. (d).

Sample No. 1 exhibits a $K_i$ of 13 nM. The low binding constant indicates that the compound exhibits good high-affinity binding to certain CNS nicotinic receptors.

Example 2

Sample No. 2 is (1S,4S)-2-(5-(3-methoxyphenoxy)-3-pyridyl)-2,5-diazabicyclo[2.2.1]heptane hernigalactarate, which was prepared in accordance with the following techniques:

3-Bromo-5-(3-methoxyphenoxy)pyridine

Following a procedure similar to that described for the preparation of 3-bromo-5-(4-methoxyphenoxy)pyridine, 3-bromo-5-(3-methoxyphenoxy)pyridine was prepared using 3-methoxyphenol (2.79 g, 0.023 mole), 75% sodium hydride suspension in oil (0.72 g, 0.023 mol) in dimethylformamide (20 mL) and 3,5-dibromopyridine (3.55 g, 0.015 mol). The reaction was worked up using water (50 mL), 5 N NaOH solution (5 mL), and diethyl ether (3×50 mL), and a yellow oil (4.6 g) was obtained as crude product. This oil was purified by column chromatography on silica gel, eluting with cyclohexane-ethyl acetate (92.5:7.5, v/v). Selected fractions containing the product were concentrated via rotary evaporation to give 2.3 g (55%) of a yellow oil.

(1S,4S)-5-(5-(3-Methoxyphenoxy)-3-pyridyl)-2-(tert-butoxycarbonyl)-2,5-diazabicyclo[2.2.1]heptane In a sealed pressure tube under an argon atmosphere, 3-bromo-5-(3-methoxyphenoxy)pyridine (0.53 g, 1.9 mmol), (1S,4S)-N-(tert-butoxycarbonyl)-2,5-diazabicyclo[2.2.1]heptane (0.469 g, 2.25 mmol), tris(dibenzylideneacetone)dipalladium(0) (0.050 g, 0.056 mmol), racemic-2,2'bis(diphenylphosphino)-1,1'binaphthyl (0.070 g, 0.11 mmol), sodium tert-butoxide (0.74 g, 7.5 mmol) and toluene (20 mL) was stirred at 70° C. for 24 h. The reaction mixture was poured into water (15 mL) and extracted with diethyl ether (3×30 mL). The combined diethyl ether extracts were dried ($MgSO_4$), filtered and concentrated to a light-brown oil (1.3 g). The material was purified by chromatography on silica gel with ethyl acetate to gain a light-yellow oil (0.62 g, 83%).

1S,4S)-2-(5-(3-Methoxyphenoxy)-3-pyridyl)-2,5-diazabicyclo[2.2.1]heptane

To a stirred solution of (1S,4S)-5-(5-(3-methoxyphenoxy)-3-pyridyl)-2-tert-butoxycarbonyl)-2,5-diazabicyclo[2.2.1]heptane (0.62 g, 1.5 mmol) in anisole (3.5 mL) at 0–5° C. and under a nitrogen atmosphere, trifluoroacetic acid (2.5 mL) was added drop-wise over a 10 min period. After 0.5 h at 25° C., the solution was adjusted to pH 5 using 10% NaOH, followed by extraction with diethyl ether (1×15 mL) to remove the anisole. The aqueous portion was adjusted to pH 11 using 10% NaOH, followed by extraction with diethyl ether (3×25 mL). The combined diethyl ether extracts were dried ($Na_2SO_4$), filtered, and concentrated under vacuum to give a colorless oil (0.41 g, 82%).

(1S,4S)-2-(5-(3-Methoxyphenoxy)-3-pyridyl)-2,5-diazabicyclo[2.2.1]heptane hemigalactarate A solution of (1S,4S)-2-(5-(3-methoxyphenoxy)-3-pyridyl)-2,5-diazabicyclo[2.2.1]heptane (0.23 g, 0.70 mmol) in ethanol (3 mL) and water (2 mL) was heated at 60° C. as mucic acid (0.069 g, 0.33 mmol) was added. The mixture was heated for 30 min, then filtered through glass wool and concentrated to approximately 1 mL. The solution was added dropwise to acetone (12 mL). The precipitate was collected, washed with diethyl ether (2 mL) and dried at 45° C. for 4 h to afford 0.200 g (65%) of fine white crystals; m.p. 172° C. (d).

Sample No. 2 exhibits a $K_i$ of 4 nM. The low binding constant indicates that the compound exhibits good high-affinity binding to certain CNS nicotinic receptors.

Example 3

Sample No. 3 is (1S,4S)-2-(5-(4-fluorophenoxy)-3-pyridyl)-2,5-diazabicyclo[2.2.1]heptane dihydrochloride, which was prepared in accordance with the following techniques:

3-Bromo-5-(4-fluorophenoxy)pyridine

Sodium hydride (1.53 g of 80% in mineral oil, 51 mmol) was slowly added to a solution of 4-fluorophenol (5.6 g, 50 mmol) in DMF (100 mL) as it was stirred and cooled (ice water bath) under a nitrogen atmosphere. The resulting mixture was warmed to ambient temperature and stirred for 1 h. 3,5-Dibromopyridine (5.9 g, 25 mmol) was added and the mixture was then heated at 90° C. (bath temperature) for 62 h. The mixture was cooled, diluted with water (150 mL), poured into 5N sodium hydroxide (150 mL), and extracted with diethyl ether (2×150 mL). The combined ether extracts were washed with water, dried ($MgSO_4$), filtered and concentrated by rotary evaporation. The residue was purified by flash chromatography on silica gel, using 5% ethyl acetate: hexane as eluent, to yield 1.4 g (21%) of a colorless oil.

(1S,4S)-5-(5-(4-Fluorophenoxy)-3-pyridyl)-2-(tert-butoxyearbonyl)-2,5-diazabicyclo[2.2.1]heptane In a sealed pressure tube under a nitrogen atmosphere, 3-bromo-5-(4-fluorophenoxy)pyridine (1.4 g, 5.2 mmol), (1S,4S)-N-(tert-butoxycarbonyl)-2,5-diazabicyclo[2.2.1]heptane (1.24 g, 6.2 mmol), tris(dibenzylideneacetone)dipalladium(0) (0.1 g, 0.1 mmol), rac-2,2'-bis(diphenylphosphino)-1,1'-binaphthyl (0.125 g, 0.2 mmol), sodium tert-butoxide (1 g, 10 mmol) and anhydrous toluene (50 mL) were stirred at 90° C. for 20 h. The reaction mixture was cooled to room temperature and diluted with water (150 mL) and then extracted with diethyl ether (2×100 mL). The combined diethyl ether extracts were dried ($MgSO_4$), filtered and concentrated by rotary evaporation. The residue was purified by flash chromatography on silica gel, using a gradient of 33% to 67% ethyl acetate:hexane as eluent, to yield 1.8 g (90%) of a yellow oil.

(1S,4S)-2-(5-(4- Fluorophenoxy)-3-pyridyl)-2,5-diazabicyclo[2.2.1]heptane dihydrochloride (1S,4S)-5-(4-Fluorophenoxy)-3-pyridyl)-2-(tert-butoxycarbonyl)-2,5-diazabicyclo[2.2.1]heptane (1.8 g, 4.7 mmol) was dissolved in ethyl acetate (50 mL). The solution was saturated with HCl gas at 5° C. (ice water bath) and was allowed to stand overnight at room temperature. After evaporation of the solvent under vacuum, the residue was triturated with ether. The formed precipitate was dried under vacuum to give 1.7 g (100%) of a yellow powder.

Sample No. 3 exhibits a $K_i$ of 12 nM. The low binding constant indicates that the compound exhibits good high-affinity binding to certain CNS nicotinic receptors.

Example 4

Sample No. 4 is (1S,4S)-2-(5-(3-thieny)-3-pyridyl)-2,5-diazabicyclo[2.2.1]heptane, which was prepared in accordance with the following techniques:

5-(3-Thienyl)-3-bromopyridine

Under a nitrogen atmosphere, a mixture of 3,5-dibromopyridine (5 g, 21 mmol), distilled water (35 mL), toluene (140 mL), ethyl alcohol (35 mL), 3-thiopheneboronic acid (2.8 g, 22 mmol), sodium carbonate (4.67 g, 44.1 mmol) and tetrakis(triphenylphosphine) palladium (1.22 g, 1.05 mmol) were stirred. This black suspension was heated at 75° C. for 20 h. After cooling to room temperature, the mixture was diluted with distilled water (200 mL) and extracted with ethyl acetate (2×200 mL, then 100 mL). The combined organic phases were dried with $MgSO_4$, filtered and concentrated by rotary evaporation, producing 17 g of a purple oil. Purification by column chromatography on silica gel, using cyclohexane:ethyl acetate (95:5) as eluent, afforded 2.9 g (58%) of white crystals, mp 58° C.

(1S,4S)-5-(5-(3-Thienyl)-3-pyridyl)-2-(tert-butoxycarbonyl)-2,5-diazabicyclo[2.2.1]heptane In a sealed pressure tube under an argon, atmosphere, 5-(3-thieny-3-bromopyridine (0.37 g, 1.5 mmol), (1S,4S)-N-(tert-butoxycarbonyl)-2,5-diazabicyclo[2.2.1]heptane (0.31 g, 1.5 mmol), tris(dibenzylideneacetone)dipalladium (0) (0.030 g, 0.033 mmol), rac-2,2'-bis(diphenylphosphino)-1,1'-binaphthyl (0.375 g, 0.059 mmol), sodium tert-butoxide (0.30 g, 3.0 mmol) and toluene (15 mL) were stirred at 80°

C. for 24 h. The reaction mixture was dissolved in water (15 mL) and then extracted with diethyl ether (3×30 mL). The combined diethyl ether extracts were dried ($MgSO_4$), filtered and concentrated to a light-brown oil (0.63 g, 93%). The material was used without further purification.

(1S,4S)-2-(5-(3-Thienyl)-3-pyridyl)-2,5-diazabicyclo[2.2.1]heptane

To a stirred solution of (1S,4S)-5-(5-(3-thienyl)-3-pyridyl-2-(tert-butoxycarbonyl)-2,5-diazabicyclo[2.2.1]heptane (0.63 g, 1.4 mmol) in anisole (3.0 mL) at 0–5° C. under a nitrogen atmosphere, trifluoroacetic acid (2.0 mL, 26 mmol) was added dropwise over a 10 min period. After 0.5 h at 25° C., the solution was adjusted to pH 5 using 10% NaOH, followed by extraction with diethyl ether (1×15 mL) to remove the anisole. The aqueous portion was adjusted to pH 11 using 10% NaOH, followed by extraction with diethyl ether (3×25 mL). The combined diethyl ether extracts were dried ($Na_2SO_4$) filtered and concentrated under vacuum. Purification of the residue by column chromatography on silica gel, using chloroform:methanol:triethylamine (40:5:1) as eluent, gave a light yellow oil (124 mg, 34%).

Sample No. 4 exhibits a $K_i$ of 670 nM. The low binding constant indicates that the compound exhibits good high-affinity binding to certain CNS nicotinic receptors.

Example 5

Sample No. 5 is (1S,4S)-2-(5-benzoyl-3-pyridyl-2,5-diazabicyclo[2.2.1]heptane dihydrochloride, which was prepared in accordance with the following techniques:

3-Benzoyl-5-bromopyridine

Thionyl chloride (50 mL) was added in a slow stream to 5-bromonicotinic acid (20.2 g, 100 mmol). After the addition was complete, the mixture was refluxed for 1 h. The excess thionyl chloride was removed under vacuum and anhydrous benzene (50 mL) was added to the residue. Aluminum chloride (33 g, 250 mmol) was added to the solution at 5–10° C. The solution was allowed to warm to room temperature and then heated at reflux for 6 h. The reaction mixture was poured into a mixture of 200 g ice and 20 mL concentrated hydrochloric acid. The organic layer and an ether extract (150 mL) of the aqueous layer were discarded. The aqueous layer, containing an emulsion, was treated with 50% aqueous NaOH until the aluminum salts redissolved. After cooling, the product was extracted with chloroform (2×200 mL). The combined chloroform layers were dried ($Na_2SO_4$), filtered and concentrated. The residue was purified by flash chromatography on silica gel, using ethyl acetate:hexane (1:5) as eluent, to yield 2.5 g (9.5%) of off-white crystals; m.p. 66–68° C.

(1S,4S)-5-(5-Benzoyl-3-pyridyl)-2-(tert-butoxycarbonyl)-2,5-diazabicyclo[2.2.1]heptane In a sealed pressure tube under a nitrogen atmosphere, 3-benzoyl-5-bromopyridine (0.542 g, 2.1 mmol), (1S,4S)-N-(tert-butoxycarb- onyl)-2,5-diazabicyclo[2.2.1]heptane (0.475 g, 2.4 mmol), tris (dibenzylideneacetone)dipalladium (0) (0.04 g, 0.04 mmol), rac-2,2'-bis(diphenylphosphino)-1,1'-binaphthyl (0.05 g, 0.08 mmol), sodium tert-butoxide (0.380 g, 3.8 mmol) and anhydrous toluene (20 mL) were stirred at 90° C. for 20 h. The reaction mixture was cooled to room temperature and diluted with water (200 mL) and then extracted with diethyl ether (100 mL). The diethyl ether extract was dried ($MgSO_4$), filtered and concentrated by rotary evaporation. The residue was purified by flash chromatography on silica gel, using a gradient of 50% to 80% ethyl acetate:hexane as eluent, to yield 0.364 g (48%) of a yellow oil.

(1S,4S)-2-(5-Benzoyl-3-pyridyl)-2,5-diazabicyclo[2.2.1]heptane dihydrochloride (1S,4S)-5-(5-Benzoyl-3-pyridyl)-2-(tert-butoxycarbonyl)-2,5-diazabicyclo[2.2.1]heptane (0.360 g, 0.95 mmol) was dissolved in ethyl acetate (30 mL). The solution was saturated with HCl gas at 5° C. (ice water bath) and was allowed to stand overnight at room temperature. After evaporation of the solvent under vacuum, the residue was triturated with ether. The formed precipitate was dried under vacuum to give 0.30 g (90%) of a yellow powder.

Sample No. 5 exhibits a $K_i$ of 122 nM. The low binding constant indicates that the compound exhibits good high-affinity binding to certain CNS nicotinic receptors.

That which is claimed:

1. A compound of the formula:

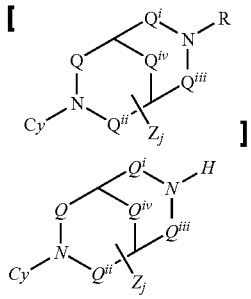

wherein:

Q is $(CH_2)_u$, $Q^i$ is $(CH_2)_v$, $Q^{ii}$ is $(CH_2)_w$, $Q^{iii}$ is $(CH_2)_x$, and $Q^{iv}$ is $(CH_2)_y$[,];

where u, v, w, and x are individually 0, 1, 2, 3, or 4; and y is 1;

wherein u, v, w, and x are selected such that the ring is a diazabicyclo [3.3.1]nonane;

Z is a substituent species G;

j is from 0 to 10; and

Cy is

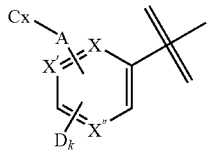

where each of X, X', and X" are individually nitrogen, nitrogen bonded to oxygen, or carbon bonded to *H or* a substituent species G;

A is O or C═O;

D is a substituent species G;

k is 0, 1, or 2; and

Cx is selected from a group consisting of aryl, substituted aryl, heteroaryl, substituted heteroaryl, non-aromatic heterocyclyl, substituted non-aromatic heterocyclyl, non-aromatic heterocyclylalkyl, and substituted non-aromatic heterocyclylalkyl[,];

wherein G is selected from the group consisting of alkyl, substituted alkyl, alkenyl, substituted alkenyl, non-aromatic heterocyclyl, substituted non-aromatic heterocyclyl, aryl, substituted aryl, heteroaryl, substituted heteroaryl, alkylaryl, substituted alkylaryl, arylalkyl, substituted arylalkyl, —F, —Cl, —Br, —I, —OR', —NR'R", —$CF_3$, —CN, —$N_3$, —$NO_2$, —C[2]≡CR', —SR', —SOR', —$SO_2CH_3$, —$SO_2$NR'R", —C(=O)NR'R", —NR'C(=O)R", NR'$SO_2$R", —C(=O)R', —C(=O)OR', —$(CH_2)_q$OR', —OC(=O)R', —(CR'R")$_q$OCH$_2$C[2]≡CR', —(CR'R")$_q$C (=O)R', —O(CR'R")$_q$C(=O)R', —C≡C(CR'R")$_q$OR', —(CR'R")$_q$NR'N", —OC(=O) NR'R", and —NR'C (=O)OR';

where R' and R" are individually hydrogen, $C_{1-8}$ alkyl, an aromatic group-containing species, or a substituted aromatic group-containing species, wherein the substituent is G and the aromatic group containing species is phenyl, biphenyl, naphthyl, pyridinyl, pyrimidinyl, quinolinyl, or indolyl[,]; and q is an integer from 1 to 6[,];

wherein heterocyclyl groups are selected from the group consisting *of* tetrahydrofuranyl, tetrahydropyranyl, tetrahydrothienyl, tetrahydrothiopyranyl, pyrrolidinyl, and piperidinyl[,]; and wherein substituted alkyl, substituted alkenyl, substituted non-aromatic heterocyclyl, substituted aryl, substituted heteroaryl, substituted alkylaryl, and substituted arylalkyl groups are alkyl, alkenyl, non-aromatic heterocyclyl, aryl, heteroaryl, alkylaryl, and arylalkyl groups [groups] further bearing one or more substituent species G.

2. The compound of claim 1, wherein X" is nitrogen.

3. The compound of claim 1, wherein X' and X" are nitrogen.

4. The compound of claim 1, wherein j is 0, 1, or 2.

5. The compound of claim 1, wherein Cx is selected from the group consisting of

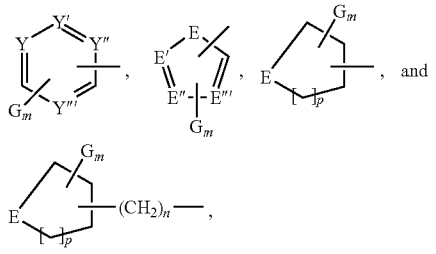

wherein:

Y, Y', Y", and Y'" are individually nitrogen, nitrogen bonded to oxygen, or carbon bonded to hydrogen or a substituent species[,] G;

E is oxygen, sulfur, or nitrogen bonded to hydrogen or a substituent species[,] G;

E', E", and E'" are individually nitrogen, or carbon bonded to hydrogen or a substituent species[,] G;

m is 0, 1, 2, 3, or 4;

p is 0, 1, 2, or 3;

n is 0, 1, 2, 3, or 4; and

G is selected from the group consisting of alkyl, substituted alkyl, alkenyl, substituted alkenyl, non-aromatic heterocyclyl, substituted non-aromatic heterocyclyl, aryl, substituted aryl, heteroaryl, substituted heteroaryl, alkylaryl, substituted alkylaryl, arylalkyl, substituted arylalkyl, —F, —Cl, —Br, —I, —OR', —NR'R", —$CF_3$, —CN, —$N_3$, —$NO_2$, —C[2]≡CR', —SR', —SOR', —$SO_2$ $CH_3$, —$SO_2$NR'R", —C(=O)NR'R", —NR'C (=O)R", NR'$SO_2$R", —C(=O)R', —C(=O) OR", —$(CH_2)_q$OR', —OC(=O)R', —(CR'R")$_q$ OCH$_2$C[2]≡CR', —(CR'R")$_q$C(=O)R', —O(CR'R")$_q$ C(=O)R', —C[2]≡C(CR'R")$_q$OR', —(CR'R")$_q$NR'N", —OC(=O)NR'R", and —NR'C(=O)OR';

where R' and R" are individually hydrogen, $C_{1-8}$ alkyl, an aromatic group-containing species, or a substituted aromatic group-containing species, wherein the aromatic group-containing species and substituted aromatic group-containing species are as defined in claim 1.

6. The compound of claim 5, wherein Y, Y', Y", and Y'" all are carbon bonded to *H or* a substituent species G.

7. The compound of claim 5, wherein one or two of Y, Y', Y", and Y'" are nitrogen and the remaining are carbon bonded to *H or* a substituent species G.

8. The compound of claim 5, wherein E', E", and E'" all are carbon bonded to *H or a* substituent species G.

9. The compound of claim 5, wherein one or two of E', E", and E'" are nitrogen and the remaining are carbon bonded to *H or a* substituent species G.

10. A compound or the formula:

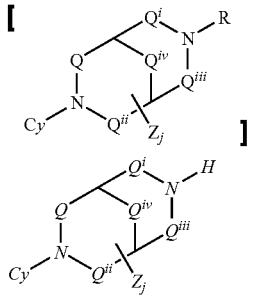

wherein:

Q is $(CH_2)_u$, $Q^i$ is $(CH_2)_v$, $Q^{ii}$ is $(CH_2)_w$, $Q^{iii}$ is $(CH_2)_x$, and $Q^{iv}$ is $(CH_2)_y$[,];

where u, v, w, and x are individually 0, 1, 2, 3, or 4; and y is 1;

wherein u, v, w, and x are selected such that the ring is a diazabicyclo [3.3.1]nonane;

Z is a substituent species G;

j is from 0 to 10;

and Cy is

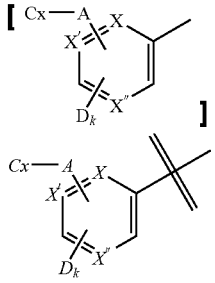

where each of X, X', and X" are individually nitrogen, nitrogen bonded to oxygen, or carbon bonded to *H or* a substituent species G;

A is a covalent bond;

D is a substituent species G;

k is 0, 1, or 2;

Cx is selected from a group consisting of aryl, substituted aryl, heteroaryl, substituted heteroaryl, non-aromatic heterocyclyl, substituted non-aromatic heterocyclyl, non-aromatic heterocyclylalkyl, and substituted non-aromatic heterocyclylalkyl;

G is selected from the group consisting of alkyl, substituted alkyl, alkenyl, substituted alkenyl, non-aromatic heterocyclyl, substituted non-aromatic heterocyclyl, aryl, substituted aryl, heteroaryl, substituted heteroaryl, alkylaryl, substituted alkylaryl, arylalkyl, substituted arylalkyl, —F, —Cl, —Br, —I, —OR', —NR'R", —$CF_3$, —CN, —$N_3$, —$NO_2$, —C[$_2$]═CR', —SR', —SOR', —$SO_2CH_3$, —$SO_2$NR'R", —C(═O)NR'R", —NR'C(═O)R", NR'$SO_2$R", —C(═O)R', —C(═O)OR", —$(CH_2)_q$OR', —OC(═O)R', —$(CR'R")_q$ $OCH_2$C[$_2$]═CR', —$(CR'R")_q$C(═O)R', —O$(CR'R")_q$ C(═O)R', —C[$_2$]═C$(CR'R")_q$OR', —$(CR'R")_q$NR'N", —OC(═O) NR'R", and —NR'C(═O)OR';

where R' and R" are individually hydrogen, $C_{1-8}$ alkyl, an aromatic group-containing species, or a substituted aromatic group-containing species, wherein the substituent is G and the aromatic group containing species is phenyl, biphenyl, naphthyl, pyridinyl, pyrimidinyl, quinolinyl, or indolyl[.];

and q is an integer from 1 to 6[.];

wherein heterocyclyl groups are selected from the group consisting of tetrahydrofuranyl, tetrahydropyranyl, tetrahydrothienyl, tetrahydrothiopyranyl, pyrrolidinyl, and piperidinyl[.]; and wherein substituted alkyl, substituted alkenyl, substituted non-aromatic heterocyclyl, substituted aryl, substituted heteroaryl, substituted alkylaryl, and substituted arylalkyl groups are alkyl, alkenyl, non-aromatic heterocyclyl, aryl, heteroaryl, alkylaryl, and arylalkyl groups [groups] further bearing one or more substituent species G.

11. The compound of claim 10 wherein X" is nitrogen.

12. The compound of claim 10, wherein X' and X" are nitrogen.

13. The compound of claim 10, wherein j is 0, 1, or 2.

14. The compound of claim 10, wherein Cx is selected from the group consisting of

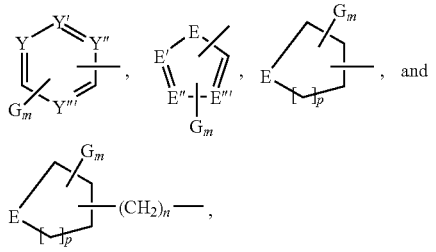

wherein:

Y, Y', Y", and Y'" are individually nitrogen, nitrogen bonded to oxygen, or carbon bonded to hydrogen or a substituent species[.] G;

E is oxygen, sulfur or nitrogen bonded to hydrogen or a substituent species[.] G;

E', E", and E'" are individually nitrogen or carbon bonded to hydrogen or a substituent species[.] G;

m is 0, 1, 2, 3, or 4;

p is 0, 1, 2, or 3;

n is 0, 1, 2, 3, or 4; and

G is selected from the group consisting of alkyl, substituted alkyl, alkenyl, substituted alkenyl, non-aromatic heterocyclyl, substituted non-aromatic heterocyclyl, aryl, substituted aryl, heteroaryl, substituted heteroaryl, alkylaryl, substituted alkylaryl, arylalkyl, substituted arylalkyl, —F, —Cl, —Br, —I, —OR', —NR'R", —$CF_3$, —CN, —$N_3$, —$NO_2$, —C[$_2$—]═CR', —SR', —SOR', —$SO_2$ $CH_3$, —$SO_2$NR'R", —C(═O)NR'R", —NR'C(═O)R", NR'$SO_2$R", —C(═O)R', —C(═O)OR", —$(CH_2)_q$OR', —OC(═O)R', —$(CR'R")_q$ $OCH_2$C[$_2$]═CR', —$(CR'R")_q$C(═O)R', —O$(CR'R")_q$ C(═O)R', —C[$_2$]═C$(CR'R")_q$OR', —$(CR'R")_q$NR'R", —OC(═O)NR'R", and —NR'C (═O)OR';

where R' and R" are individually hydrogen, $C_{1-8}$ alkyl, an aromatic group-containing species, or a substituted aromatic group-containing species, wherein aromatic group-containing species and substituted aromatic group-containing species are as defined in claim 10.

15. The compound of claim 14, wherein Y, Y', [Y'"] *Y"*, and Y'" all are carbon bonded to *H or* a substituent species G.

16. The compound of claim 14, wherein one or two of Y, Y', Y", and Y'" are nitrogen and the remaining are carbon bonded to *H or* a substituent species G.

17. The compound of claim 14, wherein E', E", and E'" all are carbon bonded to *H or a* substituent species G.

18. The compound of claim 14, wherein one or two of E', [E'] *E"*, and E'" are nitrogen and the remaining are carbon bonded to *H or a* substituent species G.

19. A pharmaceutical composition useful for treatment of central nervous system disorders comprising a therapeutically effective amount of a compound of the formula:

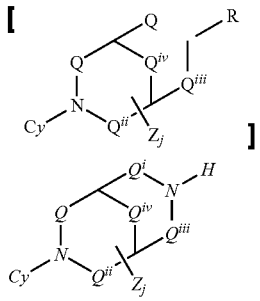

wherein Q is $(CH_2)_u$, $Q^i$ is $(CH_2)_v$, $Q^{ii}$ is $(CH_2)_w$, $Q^{iii}$ is $(CH_2)_x$, and $Q^{iv}$ is $(CH_2)_y$[.];

where u, v, w, and x are individually 0, 1, 2, 3, or 4; and y is 1 or 2;

wherein u, v, w, and x are selected such that the ring is a diazabicyclo[3.3.1]nonane;

Z is a substituent species G;

j is from 0 to 10; and

Cy is

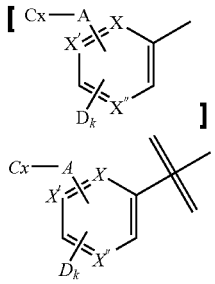

where each of X, X', and X" are individually nitrogen, nitrogen bonded to oxygen, or carbon bonded to *H or* a substituent species G;

A is O or C═O;

D is a substituent species G;

k is 0, 1, or 2; and

Cx is selected from a group consisting of aryl, substituted aryl, heteroaryl, substituted heteroaryl, non-aromatic heterocyclyl, substituted non-aromatic heterocyclyl, non-aromatic heterocyclylalkyl and substituted non-aromatic heterocyclylalkyl[,];

wherein G is selected from the group consisting of alkyl, substituted alkyl, alkenyl, substituted alkenyl, non-aromatic heterocyclyl, substituted non-aromatic heterocyclyl, aryl, substituted aryl, heteroaryl substituted heteroaryl, alkylaryl, substituted alkylaryl, arylalkyl, substituted arylalkyl, —F, —Cl, —Br, —I, —OR', —NR'R", —$CF_3$, —CN, —$N_3$, —$NO_2$, —C[$_2$—]≡*C*R', —SR', —SOR', —$SO_2CH_3$, —$SO_2$NR'R", —C(═O)NR'R", —NR'C(═O)R", NR'$SO_2$R", —C(═O)R', —C(═O)OR", —$(CH_2)_q$OR', —OC(═O)R', —(CR'R")$_q$OCH$_2$C[$_2$]≡*C*R', —(CR'R")$_q$C(═O)R', —O(CR'R")$_q$C(═O)R', —C[$_2$]≡*C*(CR'R")$_q$OR', —(CR'R")$_q$NR'N", —OC(═O)NR'R", and —NR'C(═O)OR';

where R' and R" are individually hydrogen, $C_{1-8}$ alkyl, an aromatic group-containing species, or a substituted aromatic group-containing species, wherein the substituent is G and the aromatic group containing species is phenyl, biphenyl, naphthyl, pyridinyl, pyrimidinyl, quinolinyl, or indolyl[,]; and q is an integer from 1 to 6[,];

wherein heterocyclyl groups are selected from the group consisting of tetrahydrofuranyl, tetrahydropyranyl, tetrahydrothienyl, tetrahydrothiopyranyl, pyrrolidinyl, and piperidinyl[,]; and wherein substituted alkyl, substituted alkenyl, substituted non-aromatic heterocyclyl, substituted aryl, substituted heteroaryl, substituted alkylaryl, and substituted arylalkyl groups are alkyl, alkenyl, non-aromatic heterocyclyl, aryl, heteroaryl, alkylaryl, and arylalkyl groups [groups] further bearing one or more substituent species G.

20. The pharmaceutical composition of claim 19, wherein X" is nitrogen.

21. The pharmaceutical composition of claim 19, wherein X' and X" are nitrogen.

22. The pharmaceutical composition of claim 19, wherein j[,] is 0, 1, or 2.

23. The pharmaceutical composition of claim 19, wherein Cx is selected from the group consisting of

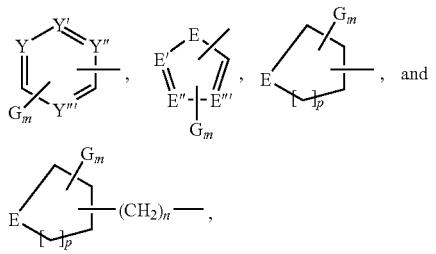

wherein:

Y, Y', Y", and Y'" are individually nitrogen, nitrogen bonded to oxygen, or carbon bonded to hydrogen or a substituent species[,] G;

E is oxygen, sulfur, or nitrogen bonded to hydrogen or a substituent species[,] G;

E', E", and E'" are individually nitrogen or carbon bonded to hydrogen or a substituent species[,] G;

m is 0, 1, 2, 3, or 4;

p is 0, 1, 2, or 3;

n is 0, 1, 2, 3, or 4; and

G is selected from the group consisting of alkyl, substituted alkyl, alkenyl, substituted alkenyl, non-aromatic heterocyclyl, substituted non-aromatic heterocyclyl, aryl, substituted aryl, heteroaryl, substituted heteroaryl, alkylaryl, substituted alkylaryl, arylalkyl, substituted arylalkyl, —F, —Cl, —Br, —I, —OR', —N[R'"]*R'R"*, —$CF_3$, —CN, —$N_3$, —$NO_2$, —C[$_2$]≡*C*R', —SR', —SOR', —$SO_2$ $CH_3$, —$SO_2$ NR'R", —C(═O)NR'R", —NR'C(═O)[R"]*R"*, —NR'$SO_2$[R"]*R'*, —C(═O)R', —C(═O)OR", —$(CH_2)_q$OR', —OC(═O)R', —(CR'R")$_q$OCH$_2$C[$_2$]≡*C*R', —(CR'R")$_q$C(═O)R', —O(CR'R")$_q$C(═O)R', —C[$_2$]≡*C*(CR'R")$_q$OR', —(CR'R")$_q$NR'N", —OC(═O)NR'R", and —NR'C(═O)OR';

where R' and R" are individually hydrogen, $C_{1-8}$ alkyl, an aromatic group-containing species, or a substituted aromatic group-containing species, wherein aromatic group-containing species and substituted aromatic group-containing species are as defined in claim 19.

24. The pharmaceutical composition of claim 23, wherein Y, Y', Y", and Y'" all are carbon bonded to *H or* a substituent species G.

25. The pharmaceutical composition of claim 23, wherein one or two of Y, Y', Y", and Y'" are nitrogen and the remaining are carbon bonded to *H or* a substituent species G.

26. The pharmaceutical composition of claim 23, wherein E', E", and E'" all are carbon bonded to *H or a* substituent species G.

27. The pharmaceutical composition of claim 23, wherein one or two of E', E", and E'" are nitrogen and the remaining are carbon bonded to *H or a* substituent species G.

28. A pharmaceutical composition useful for treatment of central nervous system disorders comprising a therapeutically effective amount of a compound of the formula:

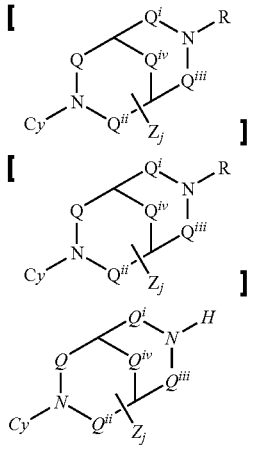

wherein:

Q is $(CH_2)_u$, $Q^i$ is $(CH_2)_v$, $Q^{ii}$ is $(CH_2)_w$, $Q^{iii}$ is $(CH_2)_x$, and $Q^{iv}$ is $(CH_2)_y$[,];

where u, v, w, and x are individually 0, 1, 2, 3, or 4; and y is 1;

wherein u, v, w, and x are selected such that the ring is a diazabicyclo [3.3.1]nonane;

Z is a substituent species G;

j is from 0 to 10; and

Cy is

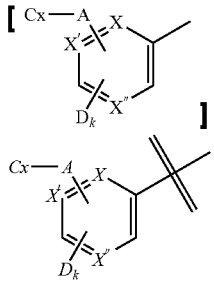

where each of X, X', and X" are individually nitrogen, nitrogen bonded to oxygen, or carbon [banded] *bonded* to *H or* a substituent species G;

A is a covalent bond;

D is a substituent species G;

k is 0, 1, or 2;

Cx is selected from a group consisting of aryl, substituted aryl, heteroaryl, substituted heteroaryl, non-aromatic heterocyclyl, substituted non-aromatic heterocyclyl, non-aromatic heterocyclylalkyl and substituted non-aromatic heterocyclylalkyl;

G is selected from the group consisting of alkyl, substituted alkyl, alkenyl, substituted alkenyl, non-aromatic heterocyclyl, substituted non-aromatic heterocyclyl, aryl, substituted aryl, heteroaryl, substituted heteroaryl, alkylaryl, substituted alkylaryl, arylalkyl, substituted arylalkyl, —F, —Cl, —Br, —I, —OR', —NR'R", —$CF_3$, —CN, —$N_3$, —$NO_2$, —C[,]═CR', —SR', —SOR', —$SO_2CH_3$, —$SO_2$NR'R", —C(═O)NR'R", —NR'C(═O)R", NR'$SO_2$R", —C(═O)R', —C(═O)OR", —$(CH_2)_q$OR', —OC(═O)R', —$(CR'R")_q$ $OCH_2$C[,]═CR', —$(CR'R")_q$C(═O)R', —O$(CR'R")_q$ C(═O)R', —C[,]═C$(CR'R")_q$OR', —$(CR'R")_q$NR'N", —OC(═O)NR'R", and —NR'C(═O)OR';

where R' *and* R" are individually hydrogen, $C_{1-8}$ alkyl, an aromatic group-containing species, or a substituted aromatic group-containing species, wherein the substituent is G and the aromatic group containing species is phenyl, biphenyl, naphthyl, pyridinyl, pyrimidinyl, quinolinyl, or indolyl[,]; and q is an integer from 1 to 6[,];

wherein heterocyclyl groups are selected from the group consisting of tetrahydrofuranyl, tetrahydropyranyl, tetrahydrothienyl, tetrahydrothiopyranyl, pyrrolidinyl, and piperidinyl[,]; and wherein substituted alkyl, substituted alkenyl, substituted non-aromatic heterocyclyl, substituted aryl, substituted heteroaryl, substituted alkylaryl, and substituted arylalkyl groups are alkyl, alkenyl, non-aromatic heterocyclyl, aryl, heteroaryl, alkylaryl, and arylalkyl groups [groups] further bearing one or more substituent species G.

29. The pharmaceutical composition of claim 28, wherein Cx is selected from the group consisting of

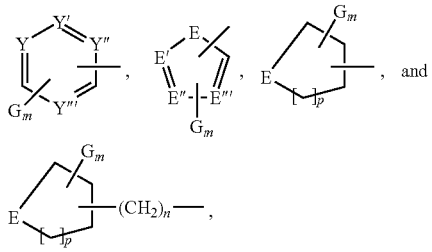

wherein:

Y, Y', Y", and Y'" are individually nitrogen, nitrogen bonded to oxygen, or carbon bonded to hydrogen or a substituent species[,] G;

E is oxygen, sulfur or nitrogen bonded to hydrogen or a substituent species[,] G;

E', E", and E'" are individually nitrogen or carbon bonded to hydrogen or a substituent species[,] G;

m is 0, 1, 2, 3, or 4;

p is 0, 1, 2, or 3;

n is 0, 1, 2, 3, or 4; and

G is selected from the group consisting of alkyl, substituted alkyl, alkenyl, substituted alkenyl, non-aromatic heterocyclyl, substituted non-aromatic heterocyclyl, aryl, substituted aryl, heteroaryl, substituted heteroaryl, alkylaryl, substituted alkylaryl, arylalkyl, substituted arylalkyl, —F, —Cl, —Br, —I, —OR', —NR'R", —$CF_3$, —CN, —$N_3$, —$NO_2$, —C[,]═CR', —SR', —SOR', —$SO_2$ $CH_3$, —$SO_2$NR'R", —C(═O)NR'R", —NR'C(═O)R", NR'$SO_2$R", —C(═O)R', —C(═O)OR", —$(CH_2)_q$OR', —OC(═O)R', —$(CR'R")_q$ $OCH_2$C[,]═CR', —$(CR'R")_q$C(═O)R', —O$(CR'R")_q$ C(═O)R', —C[,]═C$(CR'R")_q$OR', —$(CR'R")_q$NR'N", —OC(═O)NR'R", and —NR'C(═O)OR';

where R' and R" are individually hydrogen, $C_{1-8}$ alkyl, an aromatic group-containing species, or a substituted aromatic group-containing species, wherein aromatic group-containing species and substituted aromatic group-containing species are as defined in claim 28.

30. The pharmaceutical composition of claim 29, wherein Y, Y', Y", and Y'" all are carbon bonded to *H or* a substituent species G.

31. The pharmaceutical composition of claim 29, wherein one or two of Y, Y', Y", and Y'" are nitrogen and the remaining are carbon bonded to *H or* a substituent species G.

* * * * *